United States Patent
Nishiyama et al.

(10) Patent No.: US 6,998,630 B2
(45) Date of Patent: Feb. 14, 2006

(54) METHOD AND ITS APPARATUS FOR INSPECTING PARTICLES OR DEFECTS OF A SEMICONDUCTOR DEVICE

(75) Inventors: Hidetoshi Nishiyama, Tokyo (JP); Minori Noguchi, Tokyo (JP); Yoshimasa Ooshima, Tokyo (JP); Akira Hamamatsu, Tokyo (JP); Kenji Watanabe, Tokyo (JP); Tetsuya Watanabe, Tokyo (JP); Takahiro Jingu, Tokyo (JP)

(73) Assignee: Hitachi High Technologies Corporation, (JP)

( * ) Notice: Subject to any disclaimer, the term of this patent is extended or adjusted under 35 U.S.C. 154(b) by 0 days.

(21) Appl. No.: 10/933,977

(22) Filed: Sep. 3, 2004

(65) Prior Publication Data

US 2005/0024633 A1 Feb. 3, 2005

Related U.S. Application Data

(62) Division of application No. 09/931,997, filed on Aug. 17, 2001, now Pat. No. 6,797,975.

(30) Foreign Application Priority Data

Sep. 21, 2000 (JP) .............................. 2000-291952

(51) Int. Cl.
*G01N 21/88* (2006.01)
(52) U.S. Cl. .............................. 250/559.4; 250/559.41; 250/559.45; 356/237.1; 356/237.4
(58) Field of Classification Search ........... 250/559.04, 250/559.4, 559.41–559.45, 559.47; 356/237.1, 356/237.3, 237.4, 237.5, 239.8, 335, 336, 356/338

See application file for complete search history.

(56) References Cited

U.S. PATENT DOCUMENTS

| 5,663,569 A | * | 9/1997 | Hayano ................. 250/559.45 |
| 6,384,909 B1 | * | 5/2002 | Tomita et al. ........... 356/237.1 |

* cited by examiner

*Primary Examiner*—Kevin Pyo
(74) *Attorney, Agent, or Firm*—Townsend and Townsend and Crew LLP

(57) ABSTRACT

Conventionally, a particle/defect inspection apparatus outputs a total number of detected particles/defects as the result of detection. For taking countermeasures to failures in manufacturing processes, the particles/defects detected by the inspection apparatus are analyzed. Since the inspection apparatus outputs a large number of detected particles/defects, an immense time is required for analyzing the detected particles/defects, resulting in a delay in taking countermeasures to a failure in the manufacturing processes. In the present invention, an apparatus for optically inspecting particles or defects relates a particle or defect size to a cause of failure in an inspection result. A data processing circuit points out a cause of failure from the statistics on the inspection result, and displays information on the inspection result. A failure analysis is conducted by setting a threshold for identifying a failure in each of regions on a semiconductor device or the like to statistically evaluate detected particles.

16 Claims, 21 Drawing Sheets

FIG. 18A
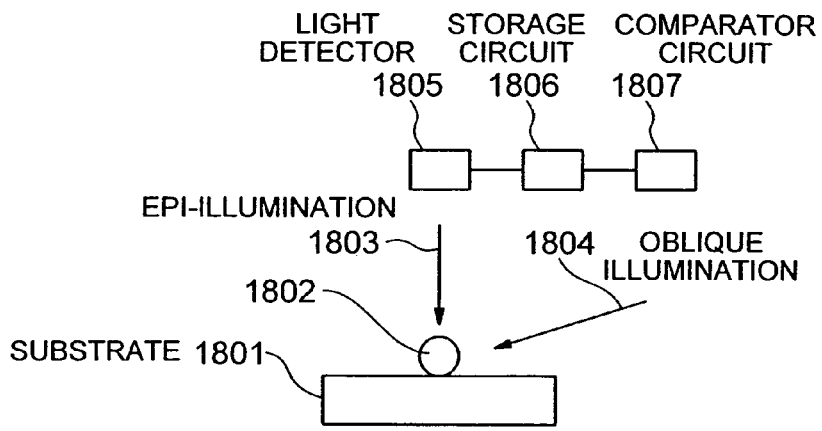
FIG. 18B
|  | DIFFERENECE IN SCATTERED LIGHT DEPENDING ON ILLUMINATING DIRECTION | | SCATTERED LIGHT AMOUNT RATIO (EPI/OBLIQUE) |
|---|---|---|---|
|  | EPI-ILLUMINATION | OBLIQUE ILLUMINATION |  |
| PARTICLES | AMOUNT OF SCATTERED LIGHT:LARGE | AMOUNT OF SCATTERED LIGHT:LARGE | SMALL |
| SCRATCHES | AMOUNT OF SCATTERED LIGHT:LARGE | AMOUNT OF SCATTERED LIGHT:SMALL | LARGE |
FIG. 19
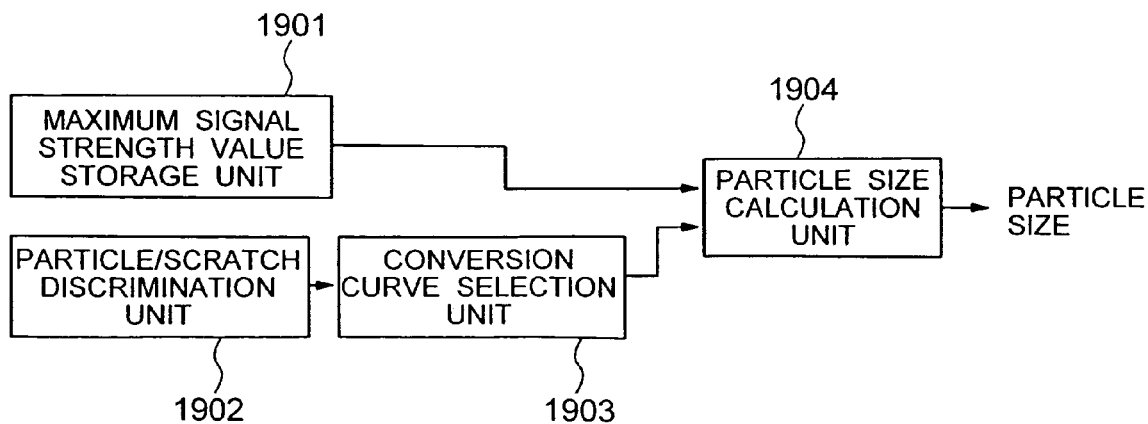

ALL PARTICLES (896)

PARTICLES OF 1.1 μm OR LARGER (311)

METHOD AND ITS APPARATUS FOR INSPECTING PARTICLES OR DEFECTS OF A SEMICONDUCTOR DEVICE

CROSS REFERENCE TO RELATED APPLICATIONS

This application is a divisional application of U.S. application Ser. No. 09/931,997, filed Aug. 17, 2001, now U.S. Pat. No. 6,797,975.

BACKGROUND OF THE INVENTION

The present invention relates to a method and apparatus for inspecting particles or defects, and more particularly, to a method and apparatus for inspecting particles or defects for use in inspecting particles existing on thin film substrates, semiconductor substrates, photomasks and so on, and pattern defects encountered on patterns on such materials, and analyzing the cause of the defects in the manufacturing of semiconductor chips and liquid crystal products, wherein the method and apparatus of the invention display an inspection result in such a form that enables the user to readily analyze the result and rapidly identify the cause of failure.

Conventionally, the technology for detecting defects on semiconductor devices and so on using an optical measuring means has been widely known. For example, "Semiconductor Wafer Inspection Apparatus" described in JP-A-62-89336 discloses a technique for irradiating a semiconductor substrate with a laser to detect scattered light from particles, if attached on the semiconductor substrate, and comparing the detected scattered light with the result of an inspection, which has been made immediately before on the same type of semiconductor substrate, to inspect the particles or defects.

Also, "Method and Apparatus for Measuring Information on Particle or Defect Size" described in JP-A-5-273110 discloses a method of measuring sizes of particles or crystal defects, which involves irradiating an object under inspection with a laser beam, receiving scattered light from possible particles or crystal defects on the object under inspection, and processing the scattered light to generate an image of the object under inspection on which the sizes of particles and crystal defects are measured.

Also, "Yield Monitoring and Analysis in Semiconductor Manufacturing" in prescripts of VLSI technology Seminar, pp. 4-42–4-47, in SEMICON Kansai, 1997, discloses an approach for analyzing the yield from particles detected on a semiconductor wafer.

Conventionally, as an approach for managing product manufacturing processes in manufacturing lines for semiconductor substrates, thin film substrates and so on, a management approach is employed for monitoring particles and defects on substrates. Such a monitoring method involves inspecting particles or pattern defects on substrates by use of an apparatus for inspecting particles or defects, monitoring a transition of the number of particles or defects detected by the inspection apparatus, and conducting a failure analysis on the particles or defects on substrates, from which a large number of particles or defects have been detected.

However, this prior art approach requires a total time for the failure analysis equal to the product of the number of detected particles/defects and a time required for the failure analysis on one particle/defect. Particularly, the failure analysis requires a prohibitively long time when the particle/defect inspection apparatus detects a large number of particles or defects, thereby giving rise to a problem that the manufacturing of substrates is delayed.

SUMMARY OF THE INVENTION

The present invention has been made to solve the problem of the prior art as mentioned above, and provides a method and apparatus for inspecting particles or defects for use in inspection and failure analysis on processes for manufacturing semiconductor wafers and thin film substrates, which are capable of performing an inspection in accordance with sizes of particles and pattern defects or the characteristics of each region on an object under inspection to take prompt countermeasures to a failure.

Specifically, the present invention provides a particle/defect inspection apparatus for measuring an object under inspection in accordance with an optical approach to detect particles or defects thereon. The inspection apparatus includes illuminating means for illuminating light to an object under inspection, light detecting means for detecting reflected light or scattered light from the object under inspection, detecting means for detecting particles or defects based on a signal detected by the light detecting means, dimension measuring means for processing the signal detected by the light detecting means to measure the size of each particle or defect, data processing means for processing an inspection result, and display means for displaying information on the inspection result, wherein the data processing means relates a particle or defect size to a cause of failure to point out the cause of failure from statistical processing on the inspection result, and the display means displays information on the inspection result.

The present invention also provides a particle/defect inspecting method for measuring an object under inspection in accordance with an optical approach to detect particles or defects thereon. The inspecting method includes a procedure for illuminating light to an object under inspection, a procedure for detecting reflected light or scattered light from the object under inspection, a procedure for detecting particles or defects based on a detected signal, a procedure for processing the detected signal to measure the size of each particle or defect, a data processing procedure for processing an inspection result, and a procedure for displaying information on the inspection result. The procedures are executed in this order to relates a particle or defect size to a cause of failure, wherein the data processing procedure points out a cause of failure from statistical processing on the inspection result to display information on the inspection result.

These and other objects, features and advantages of the invention will be apparent from the following more particular description of preferred embodiments of the invention, as illustrated in the accompanying drawings.

BRIEF DESCRIPTION OF THE DRAWINGS

FIG. 18A is a block diagram generally illustrating the configuration of an inspection apparatus which has a function of distinguishing particles from scratches;

FIG. 18B is a diagram for explaining a method of distinguishing particles from scratches;

FIG. 19 is a block diagram illustrating a method of calculating the particle size when using the method of distinguishing particles from scratches;

FIG. 30A shows a correlation of particle sizes measured on a wafer having a one-layer pattern to particle sizes measured by SEM, and FIG. 30B is a graph showing a correlation of particle sizes measured on a wafer having a multi-layer pattern to particle sizes measured by SEM;

DESCRIPTION OF THE EMBODIMENTS

In the following, each of embodiments according to the present invention will be described with reference to the accompanying drawings.

[Configuration and Operation of Apparatus for Inspecting Particles or Defects according to the Present Invention]

First, the configuration and operation of an apparatus for inspecting particles or defects according to the present invention will be described with reference to FIGS. 1 and 2.

Figure 1:
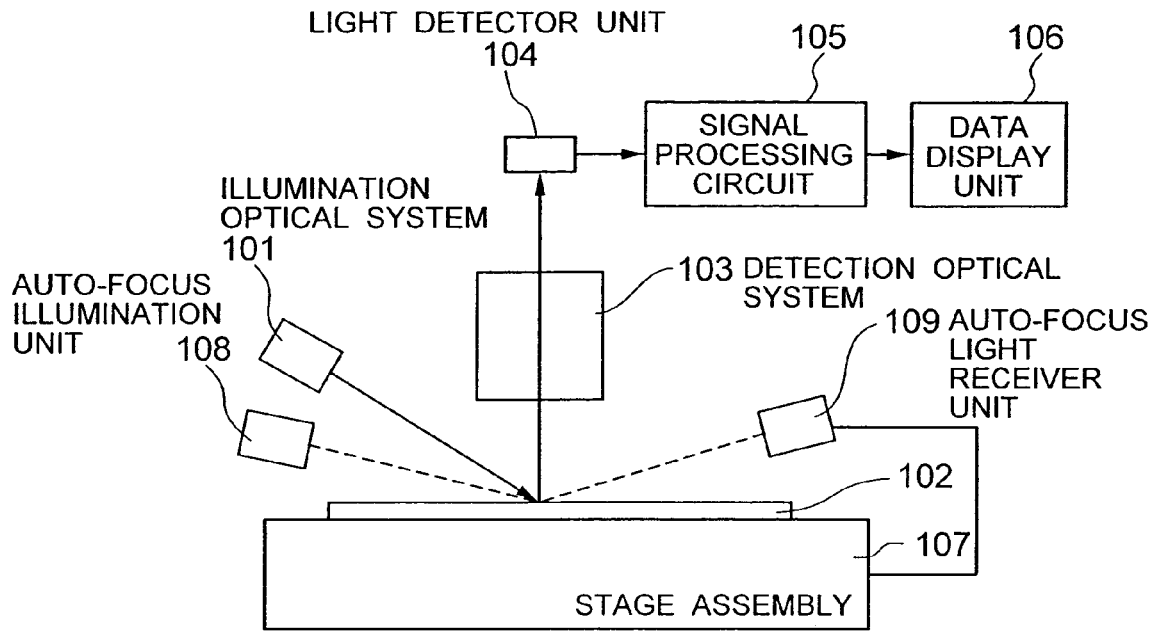
FIG. 1 is a block diagram generally illustrating the configuration of an apparatus for inspecting particles or defects according to the present invention.

FIG. 1 is a block diagram illustrating the configuration of the apparatus for inspecting particles or defects according to the present invention.

Figure 2:
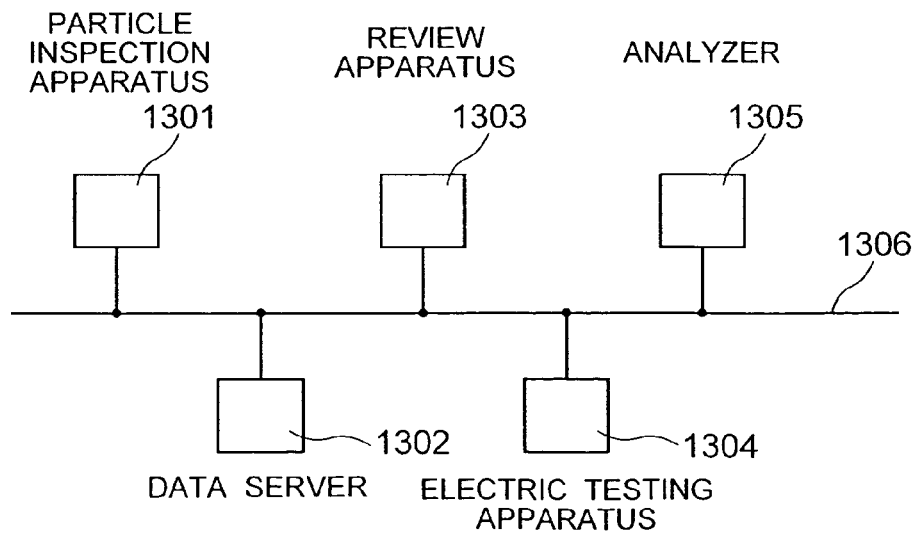
FIG. 2 is a block diagram of the apparatus for inspecting particles or defects according to the present invention when it is operated as a component of a system.

FIG. 2 is a block diagram of the apparatus for inspecting particles or defects according to the present invention when it is operated as a component of a system.

While the following description on the embodiment will be made on an example in which a semiconductor wafer is inspected for particles possibly attached thereon, the present invention can be applied to an apparatus for inspecting pattern defects other than particles. Also, the present invention is not limited to semiconductor wafers but can be applied to thin film substrates, photomasks, TFT, PDP and so on.

The apparatus for inspecting particles or defects according to the present invention comprises an illumination optical system 101; a detection optical system 103; a light detector unit 104; a signal processing circuit 105; a data display unit 106; a stage assembly 107; an auto-focus illumination unit 108; and an auto-focus light receiver unit 109.

For conducting an inspection, an object under inspection 102 is placed on the stage assembly 107 and irradiated by the illumination optical system 101, and scattered light from the object under inspection 102 is condensed by the detection optical system 103. Then, the light detector unit 104 detects the scattered light from the object under inspection 102. The scattered light detected by the light detector unit 104 is optoelectrically transduced, and processed by the signal processing circuit 105 to detect particles and measure their sizes.

The object under inspection 102 is moved in the horizontal direction by the stage assembly 107, and also moved in the vertical direction by the auto-focus illumination unit 108 and auto-focus light receiver unit 109 such that the object under inspection 102 is positioned at the focal point of the detection optical system 103. Thus, particles can be detected and their sizes be measured over the entire area of the object under inspection 102. Then, the result of detection is displayed on the data display unit 106.

Here, the illumination optical system 101 is configured to irradiate the object under inspection 102 with light, for example, from a laser light source such as Ar laser, semiconductor laser, YAG laser and UV laser, or a white light source such as an Xe lamp and Hg lamp, using a beam expander, a collimator lens, a cylindrical lens or the like. The illumination optical system 101 is adjusted such that the light is irradiated at the focal point of the detection optical system 103.

Here, for selecting an appropriate light source, a light source having a short wavelength is preferred as the illumination light source for improving the sensitivity for detecting particles, so that a YAG laser, Ar laser and UV laser are suitable. Alternatively, for reducing the size and cost of the apparatus, a semiconductor laser is suitable. Further alternatively, a white light source is suitable as the illumination light source for reducing interference by an optically transparent thin film which may be formed on an object under inspection.

As to the shape of irradiating light, a circular illumination or a liner illumination may be used for irradiation. The illumination light may be or may not be collimated light. For increasing the amount of light on an object under inspection per unit area, the power of the illumination light source may be increased, or the illumination light may be illuminated with high numerical aperture (NA).

Next, the detection optical system 103 has optical lenses configured such that from the light emitted from the illumination optical system 101, scattered light from the object under inspection 102 is condensed on the light detector unit 104. Also, the detection optical system 103 also has the ability to optically process the scattered light, for example, make modification, adjustment and so on to the optical characteristics of the scattered light using a polarizer and a spatial filter.

When a polarizer is used for optical processing, the polarizer is preferably set up in a direction in which P-polarized light is transmitted when S-polarized light is irradiated. On the other hand, the polarizer is preferably set up on a direction in which S-polarized light is transmitted when P-polarized light is irradiated. When a spatial filter is used, collimated light is suitably used as the illumination light for improving the performance of detecting particles.

The light detector unit 104 is used to receive the scattered light condensed by the detection optical system 103 for opto-electrically transducing the scattered light, and is implemented, for example, by a TV camera, a CCD linear sensor, a TDI sensor, an anti-blooming TDI sensor, and a photomultiplier.

For selecting a device for the light detector unit 104, a photomultiplier is suitable in use for detecting feeble light. Alternatively, a TV camera is suitable for rapidly capturing a two-dimensional image. When the detection optical system 103 comprises a focusing system, a TV camera, a CCD linear sensor, a TDI sensor, or an anti-blooming TDI sensor is suitable. When the detection optical system 103 comprises a light condenser system, a photomultiplier may be used. In addition, when the light detector unit 104 receives light over a wide dynamic range, i.e., if the sensor is saturated by incident light, the sensor may be additionally provided with an anti-blooming function.

Next, the signal processing circuit 105 comprises a section for detecting particles, and a section for measuring the size of a particle. For detecting particles, the signal processing circuit 105, for example, binarizes an input signal, determines a signal equal to or larger than a binarization threshold as a particle, and outputs the result of determination. While the signal processing circuit 105 also measures particle sizes, details on associated processing will be described later. The stage assembly 107 in turn has functions of, for example, moving the object under inspection 102 in the horizontal and vertical directions, and rotating the object under inspection 102. The auto-focus illumination unit 108 converges light emitted, for example, from a white light source such as an Hg lamp or a laser light source such as He-Ne onto the object under inspection 102. Here, the wavelength of a light source used in the auto-focus illumination unit 108 is preferably different from that of a light source used in the illumination optical system 101.

Next, the auto-focus light receiver unit 109 is a section for receiving a portion of emitted from the auto-focus illumination unit 108, which is reflected from the object under inspection 102, and may comprise a sensor capable of detecting the position of light, such as a position sensor. Information acquired by the auto-focus light receiver unit 109 is sent to the stage assembly 107 for controlling the stage. While in the embodiment illustrated in FIG. 1, the illumination optical system 101 illuminates the object under inspection 102 from one direction, the illumination optical system 101 may be configured to illuminate the object under inspection 102 from two directions. Further, while the example of FIG. 1 has one each of the detection optical system 103 and detector unit 104 to detect the object under inspection 102 in one direction, the inspection apparatus may comprise two or more sets of these components such that the object under inspection 102 is detected in two or more directions.

Next, FIG. 2 illustrates a system which is configured using the apparatus for inspecting particles or defects according to the present invention. Specifically, the system comprises the particle inspection apparatus 1301 of the present invention; a data server 1302; a review apparatus 1303; an electric testing apparatus 1304; an analyzer 1305; and a network 1306 for interconnecting the respective components. In this system, the review apparatus 1303 is, for example, a measuring SEM; the electric testing apparatus 1304 is a tester; and the analyzer 1305 is an apparatus for analyzing components of particles such as EDX. The data server 1302 is a computer which can collect and accumulate inspection data from the particle inspection apparatus 1301; results of reviews from the review apparatus 1303; results of tests from the electric testing apparatus 1304; and results of analyses from the analyzer 1305. The network 1306 is a communication network, for example, based on the Ethernet.

Next described will be the operation of the system using the apparatus for inspecting particles or defects. After an inspection has been made in the particle inspection apparatus 1301, particles for which appropriate countermeasures should be taken are selected by a method as described above. Information on selected particles is added to the result of inspection by the particle inspection apparatus 1301, for example, serial numbers allocated to particles when they were detected, information on the positions of particles, information on the sizes of particles, and so on, and transmitted to the data server 1302 through the network 1306. For adding the information on the selected particles, for example, a flag may be added to the result of detection to indicate whether or not appropriate countermeasures are required. Then, for investigating particles detected by the particle inspection apparatus 1301 in greater detail, the object under testing is conveyed to the review apparatus 1303. The object under testing may be manually conveyed or mechanically conveyed.

After the object under testing has been conveyed to the review apparatus 1303, the review apparatus 1303 accesses the data server 1302 to receive the result of detection from the data server 1302 through the network 1306. Then, a review is started using the received result of detection. In this event, the particles which require countermeasures are preferentially reviewed, using the information added by the particle inspection apparatus 1301, thereby making it possible to rapidly analyze particles which can cause a failure. Similarly, the analyzer 1305 can also analyze preferentially the particles which require countermeasures based on the information added by the particle inspection apparatus 1301, thereby making it possible to rapidly advance an analysis on the cause of a failure.

These review data and result of analysis may be accumulated in the data server 1302, such that they are matched with results of testing in the electric testing apparatus 1304 to confirm whether or not a failure is eventually determined. If a failure is not eventually identified, the data server 1302 transmits data for changing the criteria for selecting particles which require countermeasures to the particle inspection apparatus 1301, so that the particle inspection apparatus 1301 changes the criteria for determining whether or not countermeasures are required, thereby making-it possible to more accurately select particles which require countermeasures and to readily take appropriate countermeasures to a failure in the semiconductor manufacturing process.

While the foregoing description has been made for an example in which data is transmitted and received through a network, the transmission/reception of data need not be performed through a network, but data may be delivered through a removable recording medium or sheets of paper on which data are printed out.

Figure 16:
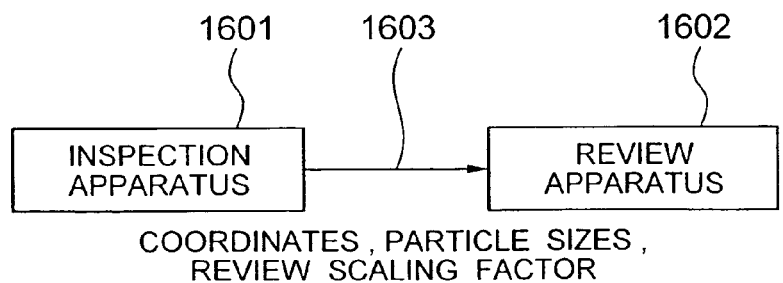
FIG. 16 is a block diagram illustrating the apparatus for inspecting particles or defects according to the present invention which is operated as a system together with a review apparatus.

Next described will be another manner of using the particle inspection apparatus 1301 according to the present invention in combination of the review apparatus 1303. FIG. 16 shows a portion of FIG. 2 extracted therefrom. In FIG. 16, an inspection apparatus 1601 is, for example, the apparatus for inspecting particles or defects of the present invention, and a review apparatus 1602, for example, a measuring SEM, reviews particles or defects on an object under inspection. Also, a network 1603 transmits/receives data between the inspection apparatus 1601 and the review apparatus 1602, and is implemented, for example, by a system connected through the Ethernet. Next, the operation will be described. It should be noted that in the following description, particles are taken as an example.

First, the inspection apparatus 1601 inspects particles on an object under inspection, and adds, for example, serial numbers allocated to particles when they are detected, information on positions of particles, and information on sizes of particles to the result of inspection. The resultant inspection data is transmitted to the review apparatus 1602 through the network 1603. After the object under inspection is conveyed to the review apparatus 1602, the particles are reviewed in the review apparatus 1602. In this event, a scaling factor for reviewing in the review apparatus may be adjusted in accordance with the information on the particle sizes measured by the inspection apparatus 1602 to perform an efficient reviewing operation. Specifically, when the particle size information acquired from the inspection apparatus 1601 shows a small particle, this particle is reviewed at a high scaling factor, so that details on the small particle can be rapidly observed. On the other hand, if the particle size information indicates a large particle, this particle is reviewed at a low scaling factor, so that the large particle can be reviewed without extending off a review screen, thereby making it possible to rapidly observe an entire image of the particle. For example, when the inspection data transmitted from the inspection apparatus 1601 indicates a particle, the size of which is 0.1 $\mu$m, this particle is reviewed by adjusting the scaling factor such that the review apparatus 1601 covers a field of view which spans 1 $\mu$m. On the other hand, when a particle has a size of 10 $\mu$m, the scaling factor is adjusted such that the review apparatus 1601 covers a field of view which spans 100 $\mu$m. In this way, the review apparatus 1602 allows the user to efficiently review small particles to large particles to rapidly analyze detected particles.

This embodiment has been described for an example in which particle size information is outputted from the inspection apparatus 1601, and the scaling factor is adjusted in accordance with the size information in the review apparatus 1602. As an alternative method, information on the review scaling factor and the field of view for reviewing in the review apparatus 1602 may be added to the inspection data.

Also, this embodiment has been described for an example in which a particle is reviewed in the field of view which spans an area ten times wider than the size of the particle by adjusting the review scaling factor for the review apparatus 1602. However, the scaling factor may be any other value. Also, if the accuracy of particle position information is known in the inspection apparatus 1601, a particle may be reviewed at a scaling factor based on the particle size information in consideration of the accuracy of the position information.

Further, while this embodiment has been described for an example in which a particle is reviewed by the review apparatus 1602, the foregoing approach may be applied when a particle is reviewed by the apparatus for inspecting particles or defects of the present invention.

[Measurement of Size of Particle]

Next, description will be made on the processing for measuring the size of a particle using the method and apparatus for inspecting particles or defects according to the present invention.

Figure 3A:
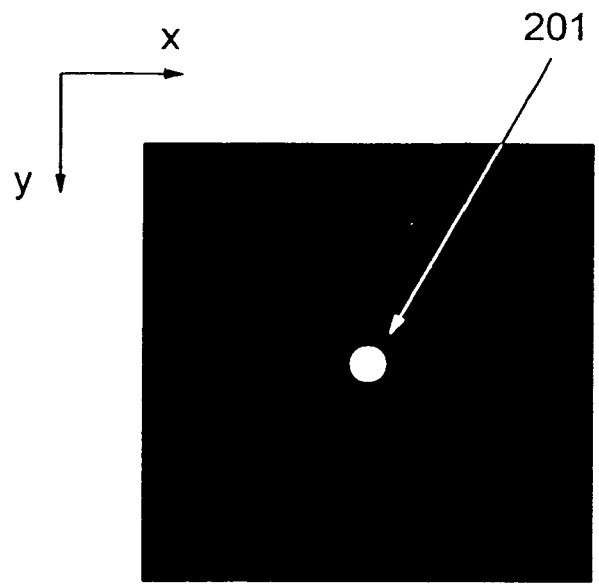
FIG. 3A is a diagram showing image data when a particle exists.
Figure 3B:
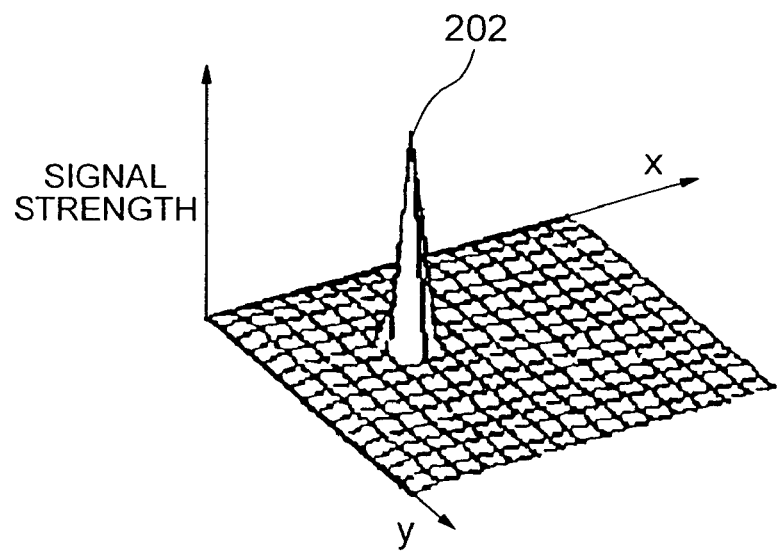
FIG. 3B is a three-dimensional graph showing a distribution of signal strength when particle data is measured.

FIGS. 3A, 3B are a diagram showing image data when a particle exists, and a diagram showing a distribution of signal strength when particle data is measured.

Figure 4A:
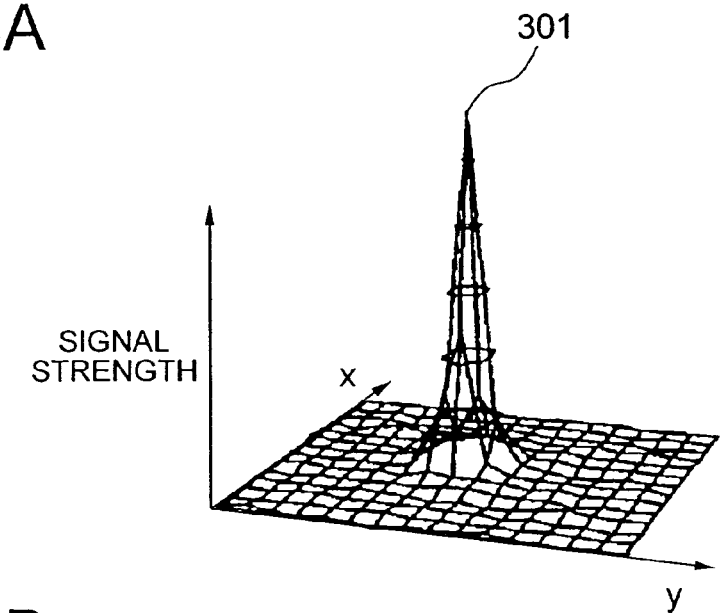
FIGS. 4A and 4B are three-dimensional graphs for comparing distributions of two types of signal strengths.
Figure 4B:
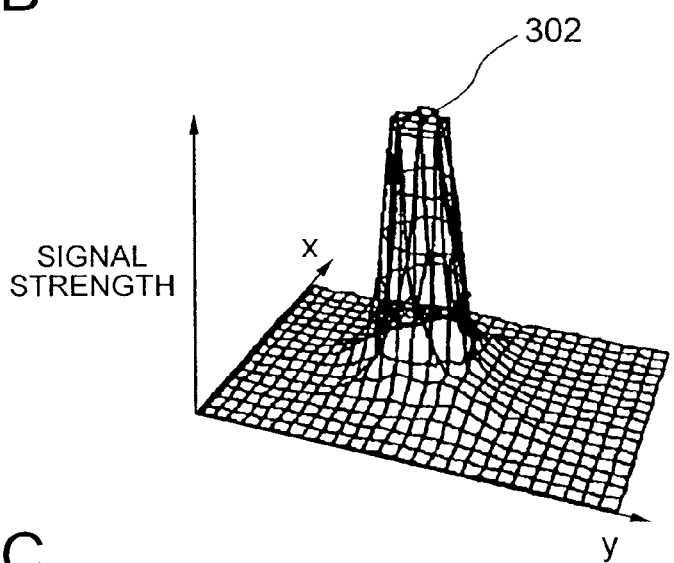
Figure 4C:
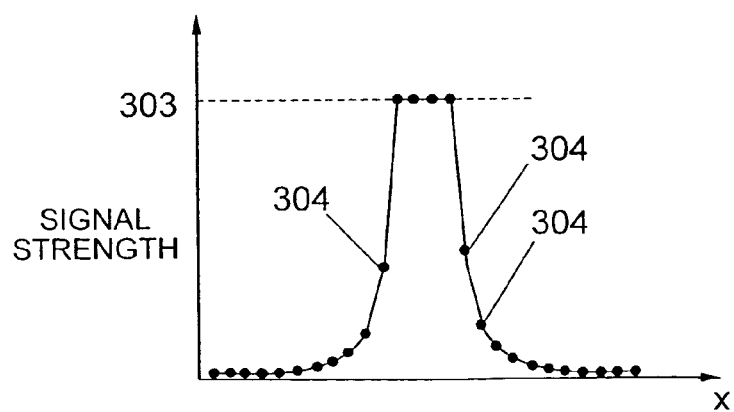
FIG. 4C is a graph for explaining how a maximum is calculated for the signal strength.

FIGS. 4A to 4C are diagrams for comparing distributions of two types of signal strengths, and an explanatory diagram for showing how a maximum is calculated for the signal strength.

FIG. 3A shows an example of image processed by the signal processing circuit 105 when a particle exists, where particle data 201 can be seen in a central portion of the image. The particle data 201 is outputted from the light detector unit 104, and captured by the signal processing circuit 105 as data having a contrast value. FIG. 3B shows FIG. 3A in a three-dimensional representation, where x- and y-axes are coordinate axes for determining a position within the image, and z-axis represents the signal strength. Signal strengths are plotted at corresponding positions, and connected by lines. In FIG. 3B, a waveform 202 indicates waveform data of the particle data 201. This waveform 202 can be approximated to a Gaussian distribution from the nature of the illumination optical system 101 and the detection optical system 103, and the width and height of the Gaussian distribution vary depending on the size of a particle on the object under inspection 102. Further, the width and height of the distribution also vary depending on the luminance of the laser illumination used in the illumination optical system 101. Therefore, the shape of a distribution and the amount of feature may have been previously measured for a variety of standard particles using the inspection apparatus of the present invention configured as described above, such that the detected waveform 202 is compared with the results of measurements made on the standard particles to acquire information on the size of the detected particle.

A method of comparing the waveform 202 of the particle with the waveforms of the standard particles may involve previously measuring the total sum (integral) of the signal strengths in the region occupied by the particle data 201, i.e., data on the volume of the waveform 202, and comparing the volume data of the particle data 201 with the volume data of the standard particles. However, if the illumination optical system 101 differs in luminance when the standard particles are measured and when particles on the object under inspection are measured, the respective volume data are divided by the luminances of the illumination optical system 101 for normalization, or the volume data of the particle data 201 or the standard particles is multiplied by the ratio of luminances to correct the volume data.

As an alternative method of comparing waveforms, a maximum signal strength value in the waveform 202 or the width of the waveform 202 may be compared.

A method of calculating a maximum signal strength value will be explained with reference to FIGS. 4A to 4C. FIGS. 4A, 4B show exemplary waveforms of particle data, similar to the waveform 202.

Specifically, FIG. 4A shows an example in which a signal waveform of particle data acquired by the light detector unit 104 is in the shape of pinnacle having a peak, indicating that the signal does not reach a saturation region of the light detector unit 104. FIG. 4B in turn shows an exemplary signal waveform of particle data which presents a plateau shape at the peak, indicating that the signal reaches the saturation region of the light detector unit 104 and does not include data exceeding the saturation region.

The maximum signal strength value is defined as the value which is determined as maximum as a result of comparison between signal strengths at respective pixels of the waveform, when particle data draws a signal waveform as shown in FIG. 4A, i.e., a signal strength at the peak point 301. On the other hand, when particle data draws a signal waveform as shown in FIG. 4B, a calculation is performed as described below to find a maximum signal strength value.

First, in the saturation region 302, maximum lengths of the saturation region are calculated in the x- and y-directions, respectively. FIG. 4C shows a cross-section of FIG. 4B taken along the maximum length region. In FIG. 4C, the horizontal axis is a coordinate axis representing the position in the maximum length region, while the vertical axis is a coordinate axis representing the signal strength. The signal strength 303 indicates the saturation level of the light detector unit 104. On this cross-section, three or more unsaturated signals 304 are selected. Here, description is made on the assumption that three points are selected. As points to be selected, three points having the largest signal strengths are selected from unsaturated signals on the cross-section. Assuming that the three points are at coordinates x1, x2, x3, and have signal strengths z1, z2, z3, respectively, equations representing Gaussian distributions are derived using unknown numbers k, σ, u:

$$z1 = k/\sigma \cdot \exp(-(x1-u)^2/(2 \cdot \sigma^2))$$

$$z2 = k/\sigma \cdot \exp(-(x2-u)^2/(2 \cdot \sigma^2))$$

$$z3 = k/\sigma \cdot \exp(-(x3-u)^2/(2 \cdot \sigma^2))$$

The unknown values k, σ, u can be found by solving the simultaneous equations. Then, the maximum signal strength value in FIG. 3B can be calculated using the resulting values of k, σ as follows:

$$k/\sigma$$

It should be noted that although the example shown herein uses the unknown value u for calculating the maximum signal strength value, the unknown value u need not be used. In this case, two points are selected from the unsaturated signals 304. Selected signal points are those having the largest signal strengths from unsaturated signals on the cross-section. Assuming that the two points are at coordinates x1, x2, and have signal strengths z1, z2, respectively, equations representing Gaussian distributions are derived using unknown numbers k, σ:

$$z1 = k/\sigma \cdot \exp(-(x1)^2/(2 \cdot \sigma^2))$$

$$z2 = k/\sigma \cdot \exp(-(x2)^2/(2 \cdot \sigma^2))$$

Since the unknown values k, σ can be found by solving the simultaneous equations, the maximum signal strength value in FIG. 3B can be calculated using the values of k, σ as follows:

$$k/\sigma$$

A particle size can be measured by comparing the maximum signal strength value derived from the foregoing calculation for a detected particle with those for the standard particles.

Next, another embodiment for calculating the maximum signal strength value will be described with reference to FIG. 17.

Figure 17A:
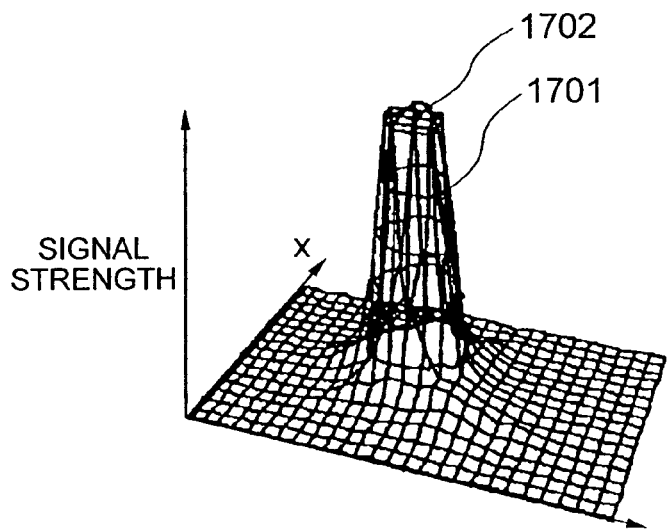
FIG. 17A is a three-dimensional graph showing a distribution of a saturated signal strength.
Figure 17B:
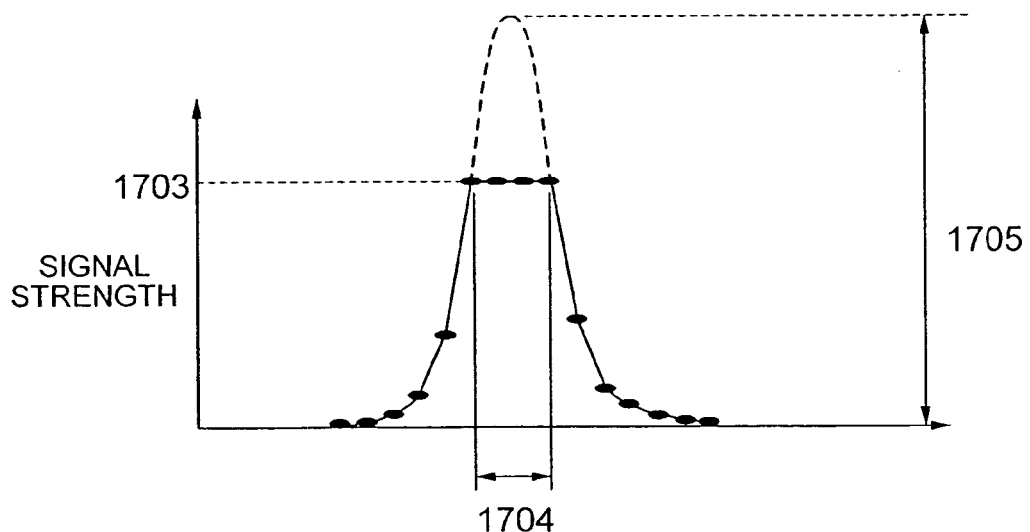
FIG. 17B is a graph for explaining how a maximum is calculated for the signal strength.
Figure 17C:
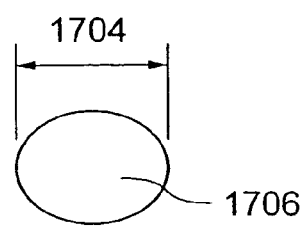
FIG. 17C is a plan view of a particle showing a major axis and a minor axis of the particle.

FIG. 17A to 17C are a graph showing a signal distribution of particle data which presents a plateau shape at the peak; a diagram showing the shape of the saturated signal portion; and an explanatory diagram for explaining how the maximum signal strength value is calculated. FIG. 17A shows the relationship between a signal waveform 1701 and a peak region 1702, wherein the peak region 1702 in the signal waveform 1701 does not include data exceeding the saturated level since the peak region 1702 reaches the saturation region of the light detector unit 104. FIG. 17B shows a cross-section of the signal waveform 1701, where the vertical axis represents the signal strength, and the horizontal axis represents the pixel position in the signal. In FIG. 17B, a saturation level 1703 indicates the saturation level of the light detector unit 104, and a signal width 1704 indicates the width of the peak region 1702. Also, a signal strength 1705 is a maximum signal strength value which is generated when an unsaturable detector is used for the light detector unit 104.

Next explained is a method of calculating the maximum signal strength value 1705 from the saturated signal waveform 1701. Assuming that the saturation level 1703 is represented by SL; the signal width 1704 by SW, and the signal strength 1705 by PL, the illustrated waveform is approximated to a Gaussian distribution to derive the following equations:

$$SL = k/\sigma \cdot \exp(-(-SW/2)^2/(2 \cdot \sigma^2))$$

$$PL = k/\sigma$$

where k is a coefficient, and σ is a value calculated from configuration of the optical system in the apparatus for inspecting particles and defects of the present invention.

Therefore, from the two equations, PL is calculated as follows:

$$PL = SL/\exp(-(-SW/2)^2/(2 \cdot \sigma^2))$$

Here, since SL indicates the output of the light detector unit 104 when it is saturated, SL represents 255 gradation levels when an A/D converter of the light detector unit 104 has a 8-bit resolution. σ is given a value from zero to one depending on the configuration of the optical system. Next, a method of calculating SW will be described. FIG. 17C shows the shape of the peak region 1702, in other words, a region in which the light detector unit 104 is saturated. FIG. 17C includes a saturation region 1706 and a signal width 1704. Since the signal waveform 1701 is regarded as a Gaussian distribution, the saturation region 1706 can be assumed to be circular. Therefore, assuming that the signal width 1704 is represented by SW, and the saturation region 1706 by SA, SW is calculated by:

$$SW = 2 \cdot \sqrt{(SA/\pi)}$$

In the above equation, $\sqrt{(A)}$ represents a calculation of a square root of A, and π is the Ludolphian number. The saturation region 1706 may be comprised of the number of pixels in which the light detector unit 104 is saturated. Here, a saturated pixel may be represented by a maximum of the output from the A/D converter of the light detector unit 104, and may be set in consideration of electric noise in the light detector unit 104. For example, when the A/D converter has an 8-bit resolution, the output represents a maximum of 255 gradation levels. It may be thought that the output at 245th gradational level or higher is saturated if electric noise accounts for 10 gradation levels.

If the signal waveform 1701 is not saturated, a similar calculation may be performed using a maximum of the signal waveform 1701 as the saturation level 1703.

Since the maximum signal strength value can be calculated from the foregoing process, the size of a detected particle can be measured by comparing the values calculated using the standard particles with a value calculated using the detected particle.

While the foregoing description has been made for the maximum signal strength value as an example, the integral of signal strength over particle data may be used instead of the maximum signal strength value. In this case, the integral of signal strength over particle data may be calculated by adding contrast values of respective pixels in the detected particle signal. Also, while the foregoing embodiment employs an 8-bit A/D converter, an A/D converter having 10 bits or more may be used. Further, while the foregoing embodiment has been described for an example of calculating the signal width 1704 as the diameter of a circle, a width of the saturation region which indicates a maximum length or a minimum length may be used instead of the diameter.

In the description on the configuration of the apparatus, the illumination optical system 101 uses laser light as an example in the foregoing embodiment. Alternatively, white light may be used instead of laser light. Also, when an object under testing has repeated circuit patterns, the foregoing measurement of the size may be made after taking a difference between an image of the repeated pattern on which no particle exists and an image of the same on which a particle exists. Also, irrespective of the presence or absence of repeated patterns, if data on scattered light or data on reflectivity associated with the circuit pattern or a film, for example, an oxide film or a metal film, can be acquired beforehand, such data may be used to correct data on the size of a particle on the circuit pattern or the film. Furthermore, while the foregoing embodiment measures the size of a particle by comparing it with the sizes of standard particles, the size of the particle may be compared with a particle, the size of which is known, instead of the standard particles.

Figure 15:
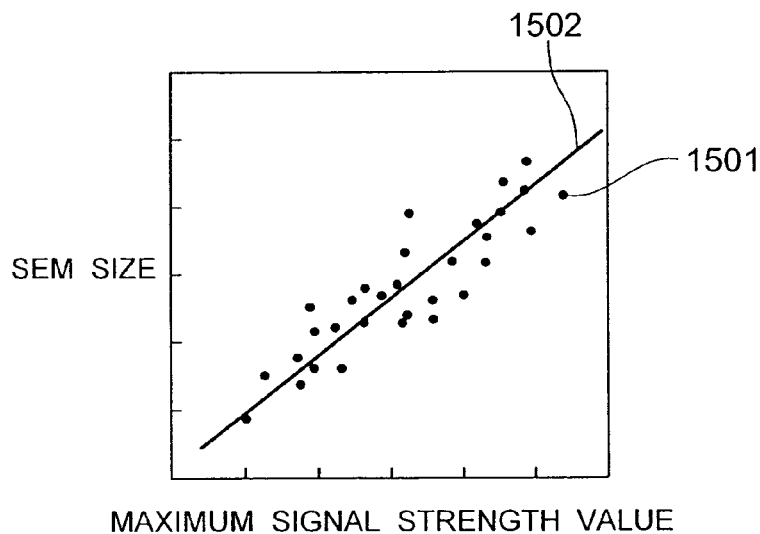
FIG. 15 is a graph for explaining the relationship between a maximum of signal strength generated by the apparatus for inspecting particles or defects according to the present invention and the particle size.

Next, an exemplary method of calculating a particle size from the maximum signal strength value will be described with reference to FIG. 15 when using data on a particle, the size of which is known. FIG. 15 is a graph in which the horizontal axis represents a maximum signal strength value of particle acquired from the apparatus for inspecting particles or defects according to the present invention, and the vertical axis represents the particle size. Here, the maximum signal strength values of particles are calculated by the aforementioned method, while the size of a particle is derived by measuring a horizontal dimension and a vertical dimension of the particle using a review apparatus such as a measuring SEM, multiplying the horizontal dimension by the vertical dimension, and taking a square root of the product. In FIG. 15, a plot point 1501 indicates data on a particle, so that FIG. 15 indicates data on a plurality of particles. An approximate curve 1502 is calculated by a least-square method based on the data at the plot points 1501. In this event, the approximate curve can be expressed by an equation $y=a \cdot x+b$ when the horizontal axis of the graph is represented by x, and the vertical axis of the same by y, where, a and b are values found by a least-square method.

For calculating a particle size from a maximum signal strength value, a relational expression between the maximum signal strength value and the particle size is found and is used to calculate the particle size from the maximum signal strength value.

Next, the operation will be described. First, the approximate curve 1502 has been previously calculated by the aforementioned method. Next, an object under inspection is inspected using the apparatus for inspecting particles or defects according to the present invention. Then, a maximum signal strength value for the particle is calculated as described above during the inspection. In this event, using the approximate curve, the maximum signal strength value is substituted into x of the approximate curve to calculate y which is determined as the particle size.

Figure 30A:
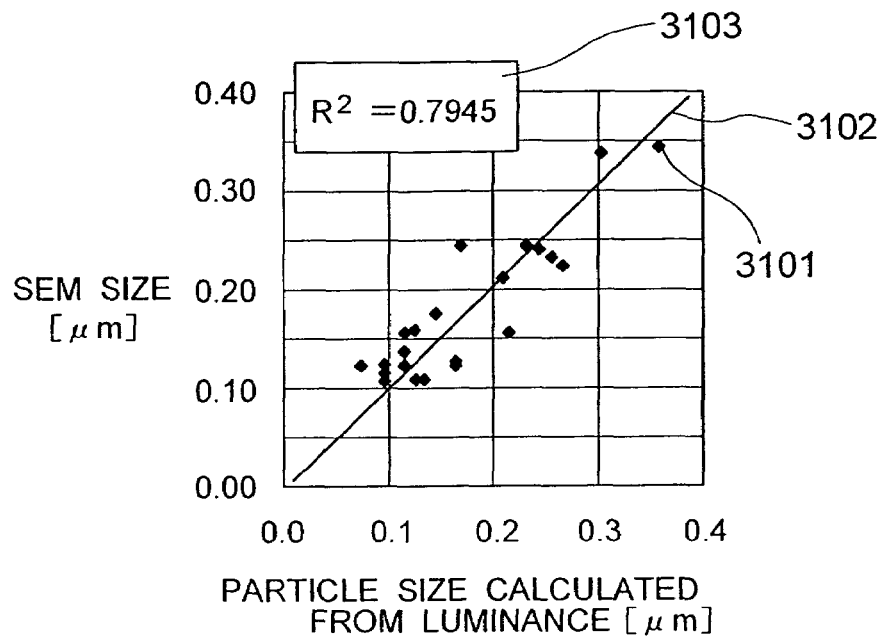
FIGS. 30A and 30B are graphs showing correlations of particle sizes measured by the apparatus for inspecting particles or defects according to the present invention to particle sizes measured by SEM, where
Figure 30B:
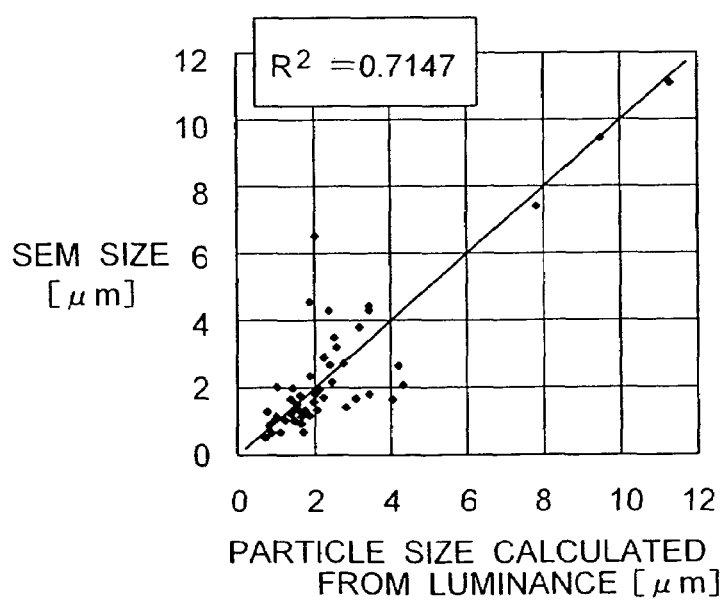
Figure 31:
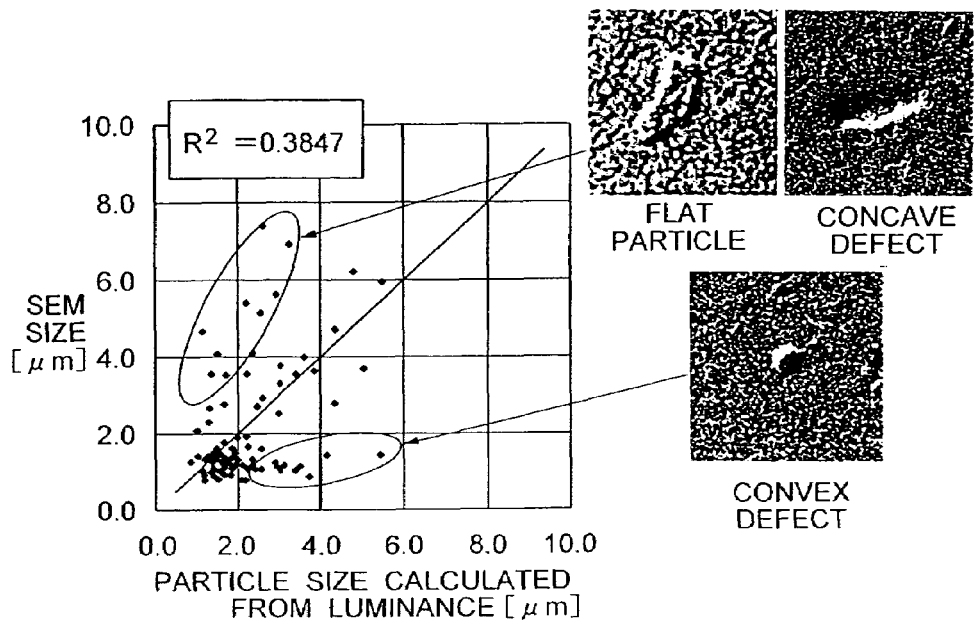
FIG. 31 includes a graph showing a correlation of particle sizes measured by the apparatus for inspecting particles or defects according to the present invention to particle sizes measured by SEM, and SEM photographs of detected particles.

Examples of the results calculated by the foregoing method are shown in FIGS. 30A, 30B and 31. FIGS. 30A, 30B are graphs, wherein the horizontal axis represents the particle size calculated from signal outputted from the apparatus for inspecting particles or defects according to the present invention, and the vertical axis represents the particle size measured by a measuring SEM. A plot point 3101 corresponds to information on one particle. A straight line 3102 in turn represents an approximate line when each of plot points 3101 is least-mean-square approximated, and a value 3103 indicates a correlation value at the plot point 3101.

Further, FIG. 30A shows the result of measuring sizes of particles detected on a wafer having a one-layer pattern, and FIG. 30B shows, by way of example, the result of measuring sizes of particles detected on a wafer having a multi-layer pattern.

FIG. 31 shows, by way of example, SEM photographs of used particles in addition to the particle sizes calculated from signals outputted from the apparatus for inspecting particles or defects according to the present invention on the horizontal axis, and the particle sizes measured by the measuring SEM on the vertical axis, in a manner similar to FIGS. 30A, 30B.

While this embodiment calculates a square root of the vertical dimension and the horizontal dimension of each particle, the size of a particle may be defined as the larger one of the vertical dimension and the horizontal dimension of the particle, or an average value of the vertical dimension and the horizontal dimension of the particle. Alternatively, the major axis of a particle may be used, or the minor axis of the particle may be used. Further, the approximate curve may be a first-order curve, i.e., a straight line, or a higher-order curve, a logarithmic curve or an exponential curve, or a combination of a plurality of curves.

If the provision of different approximate curves for respective shapes of particles results in a better correlation of the particle sizes calculated as described above to the particle sizes measured using the measuring SEM, a different approximate curve may be used for each shape of particle. Here, the difference in the shape of a particle refers to, for example, the difference between a spherical particle and a flat plate-shaped particle, or the difference between a particle and a scratch, when the difference lies in the ratio of the particle size measured from above to the particle size measured from the side.

Now, a method of distinguishing a particle from a scratch will be described with reference to FIGS. 18A, 18B. FIG. 18A illustrates the configuration for discriminating between a particle and a scratch, and FIG. 18B shows how they are discriminated. FIG. 18A comprises a substrate 1801; a particle 1802; epi-illumination light 1803 which illuminates the substrate from a perpendicular direction; oblique illumination light 1804; a light detector 1805; a storage circuit 1806; and a comparator circuit 1807. In the illustrated configuration, the epi-illumination light 1803 is emitted to the substrate at an angle close to a direction perpendicular to the surface of the substrate 1801, while the oblique illumination light 1804 is emitted to the substrate 1801 at an angle close to a direction horizontal to the substrate 1801. Their light sources may be an Ar laser, a YAG laser, or the like, by way of example. The light detector 1805, in turn, may be a TV camera, a CCD linear sensor, a TDI sensor, or a photomultiplier.

Next, the operation will be described. A particle or a scratch is irradiated with the epi-illumination light 1803 to detect scattered light from the particle or scratch by the light detector 1805. The amount of scattered light is stored in the storage circuit 1806. Subsequently, the irradiation of the epi-illumination light 1803 is stopped, and the oblique illumination light 1804 is irradiated to the particle or scratch to detect scattered light from the particle or scratch by the light detector 1805. The amount of scattered light is stored in the storage circuit 1806. Next, the light intensities, or the amounts of scattered light stored in the storage circuit 1806 are compared by the comparator circuit 1807. The comparator circuit 1807 calculates the ratio of the amount of scattered light when the epi-illumination light 1803 is irradiated to the amount of scattered light when the oblique illumination light 1804 is irradiated, and compares the ratio with a previously determined threshold to determine a particle or a scratch. A determination method used herein may take advantage of the fact that a particle has a smaller ratio of the amounts of scattered light, and a scratch has a larger ratio, as shown in FIG. 18B.

Next, a method of calculating a particle size when there are a plurality of approximate curves will be described with reference to FIG. 19. FIG. 19 comprises a storage unit 1901 for storing a maximum of detected signals; a discrimination unit 1902 for discriminating between a particle and a scratch; a conversion curve selection unit 1903; and a particle size calculation unit 1904.

Next, the operation will be described. First, a conversion equation for calculating a particle size from a maximum signal strength value using the aforementioned method has been created for each of a particle and a scratch in the apparatus of inspecting particles or defects according to the present invention and stored in the conversion curve selection unit 1903. Next, a wafer is inspected by the inspection apparatus. In this event, a maximum signal strength value of a detected substance is stored in the storage unit 1901. Next, the discrimination unit 1902 determines whether the detected substance is a particle or a scratch by the aforementioned method. Based on this determination, a conversion curve is selected from the conversion curve selection unit 1903, and the selected conversion curve and the maximum signal strength value stored in the storage unit 1901 are inputted to the particle size calculation unit 1904 to calculate the size of the particle.

While the foregoing embodiment has described for an example in which a conversion curve is set according to the shape of a particle and a defect, a different approximate curve may be used according to the position on an object under inspection at which a particle is detected, for example, whether a particle on a circuit pattern or a particle on a region without patterns. Alternatively, a different approximate curve may be used depending on the surface state of an object under inspection, for example, whether the surface is coated with an aluminum film or a tungsten film.

[Method of Calibrating Measured Particle Size]

Next described will be a method of calibrating a particle size measured by the apparatus for inspecting particles or defects according to the present invention. This calibration may be used, for example, when the amount of illumination light has changed due to a deterioration in the illumination optical system in the apparatus for inspecting particles or defects according to the present invention.

An exemplary calibrating method will be described. First, mirror wafers with standard particles having known sizes attached thereto is prepared as calibration wafers. Two or more types of standard particles are preferably prepared. For example, a standard particle of 0.2 μm and a standard particle of 0.6 μm are attached to mirror wafers, respectively. Next, these wafers are inspected by the apparatus for inspecting particles or defects according to the present invention to display the sizes of detected particles. In this event, if the inspection apparatus does not fail, peaks will appear at 0.2 μm and 0.6 μm on the scale of the histogram.

Figure 26:
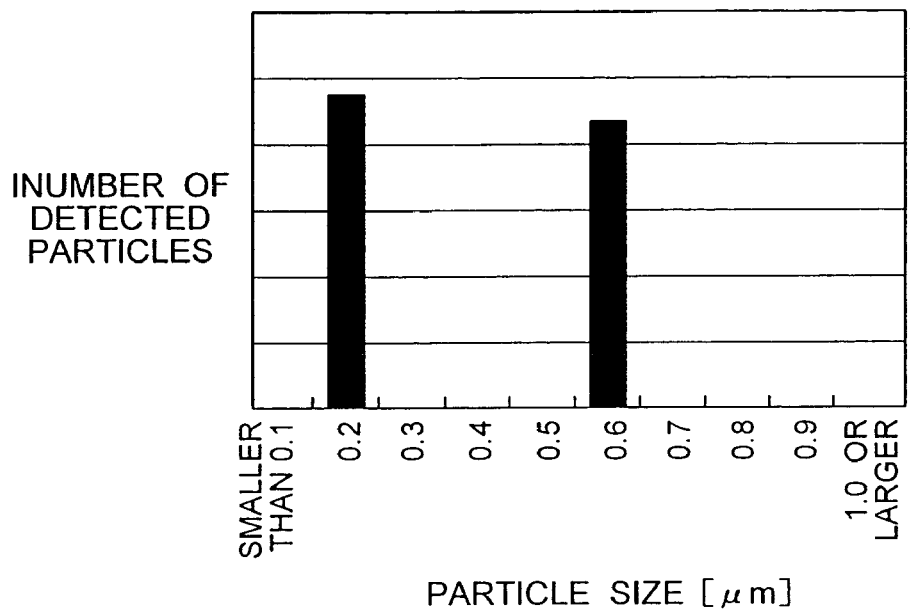
FIG. 26 is a graph showing the relationship between the particle size and the number of detected particles when standard particles are measured by the apparatus for inspecting particles or defects according to the present invention.
Figure 27:
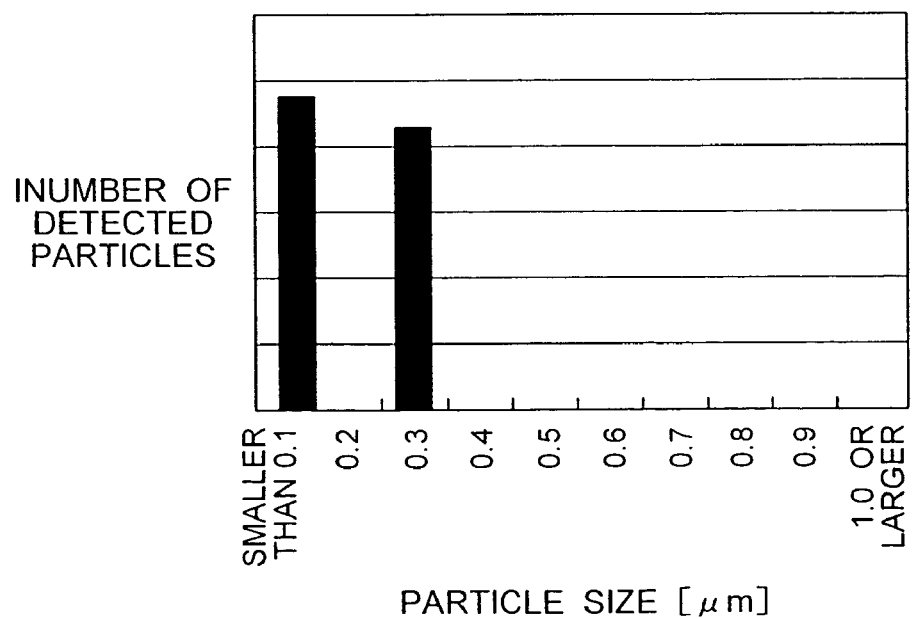
FIG. 27 is a graph showing the relationship between the particle size and the number of detected particles before calibrating the sensitivity for the size of detectable particles in the apparatus for inspecting particles or defects according to the present invention.

For example, FIG. 26 is a graph showing the number of detected particles on the vertical axis, and sizes of the detected particles on the horizontal axis. As can be seen in FIG. 26, the number of detected particles is increased at 0.2 μm and 0.6 μm on the scale. In contrast to FIG. 26, FIG. 27 shows an example when the laser light source used in the illumination optical system 101 has deteriorated to reduce the amount of illumination light to one half, wherein the number of detected particles is increased at 0.1 μm and 0.3 μm on the scale. In other words, FIG. 27 shows an example in which a reduced amount of illumination light results in a less amount of scattered light, so that particle sizes are measured smaller than correct values.

Next explained will be a method of calculating a calibration coefficient for calibrating the inspection apparatus. Assume first that the size of the standard particle inspected above is SS, and the size of a particle measured by the inspection apparatus of the present invention is IS. In this event, since a reduced amount of illumination light is calculated from the ratio of SS to IS, the calibration coefficient, designated VR, is calculated by:

$$VR=SS/IS$$

Therefore, the calibration may be accomplished by increasing the amount of illumination light by a factor of VR or by multiplying a conversion equation for calculating the a particle size from the amount of scattered light by VR. Specifically, in the aforementioned example, assuming that the size SS of the standard particle is 0.2 μm and the size IS of the particle measured by the inspection apparatus is 0.1 μm, the calibration coefficient VR is calculated as:

$$VR=2$$

so that the amount of illumination light may be increased twice.

While the foregoing example has employed a wafer with a standard particle of a known size attached thereto as a calibration wafer, the calibration wafer is only required to have a particle or a defect of known size attached thereto, so that a wafer having a defect of known size intentionally created therein may be used instead.

Next, another calibration method will be described with reference to FIG. 2.

This is a method which uses values measured by the review apparatus as particle sizes. First, an inspection is made in the particle inspection apparatus 1301, and information on selected particles is added to the results of inspection by the particle inspection apparatus 1301, for example, serial numbers allocated to particles when they were detected, information on the positions of the particles, information on the sizes of the particles, and so on, and transmitted to the data server 1302 through the network 1306. After the wafer has been conveyed to the review apparatus 1303, the wafer is reviewed by the review apparatus 1303, and information on particle sizes measured therein is added to the inspection result. Here, the particle size information is derived, when using, for example, a measuring SEM as the review apparatus 1303, by measuring the horizontal dimension and vertical dimension of a particle using the measuring SEM, multiplying the horizontal dimension by the vertical dimension, and taking a square root of the product. Next, the information added to the inspection result is transmitted to the data server 1302, and the added information is received by the particle inspection apparatus 1301 to calibrate the particle size information outputted from the particle inspection apparatus 1301 based on the size information.

Figure 28:
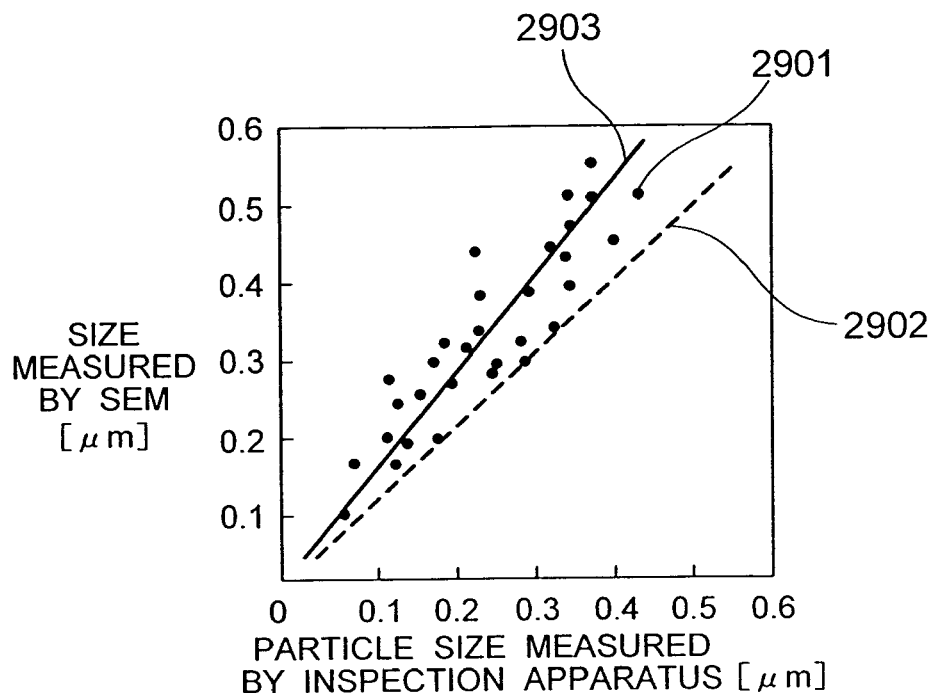
FIG. 28 is a graph showing the relationship between particle sizes measured by the inspection apparatus according to the present invention and sizes measured by SEM when the sensitivity for the size of detectable particles is calibrated in the apparatus for inspecting particles or defects according to the present invention.

The calibration method will be described with reference to FIG. 28. FIG. 28 is a graph showing the information on the size of each particle measured by the particle inspection apparatus 1301 on the horizontal axis, and the information on the size measured by the review apparatus 1303 on the vertical axis. In FIG. 28, a plot point 2901 indicates information on the size of the same particle, so that FIG. 28 plots information on a plurality of particles. Here, if the particle sizes are correctly measured, plot points 2901 should be arranged along a straight line 2902. The calibration method first finds an approximate line for the data of the plot points 2901 through a least-square method or the like. This approximate line is the straight line 2903 which is expressed by an equation:

$$y=a \cdot x+b$$

where x represents the size of a particle measured by the inspection apparatus on the horizontal axis, and y represents the size of the particle measured by the review apparatus 1303 on the vertical axis. Also, a and b are values found by a least-square method. Next, the particle is inspected by the apparatus for inspecting particles or defects according to the present invention, the size of the particle is measured, and the measured size is substituted into x in the above equation. The resulting value y is determined as the size of the particle after calibration.

While the linear approximation has been described as the calibration method, the approximation may be made to a higher order curve, a logarithmic curve, an exponential curve, or a combination of curves. In addition, a wafer for use in calibrating the particle size is not limited to one, but a plurality of wafers may be used.

In the foregoing description, particles are inspected using scattered light. This method is advantageous in that particles can be efficiently found. Also advantageously, when particle sizes are calculated by the aforementioned method, particles can be found without requiring a special light source for measuring the sizes, and measurements of the sizes can be made with scattered light from the same light source.

[Analysis on Cause of Failure and Display of Result]

Next, description will be made on a procedure for analyzing a cause of failure and a procedure for displaying the result of analysis to the user when particle sizes are measured using the apparatus for inspecting particles or defects according to the present invention.

Figure 5A:
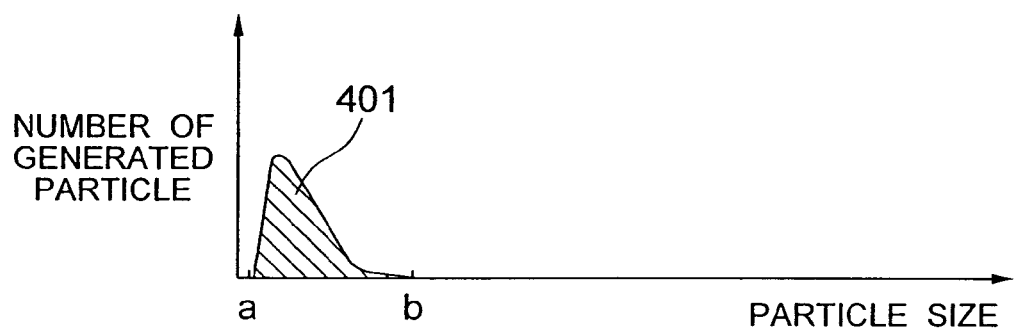
FIGS. 5A to 5C are graphs showing the relationship between the particle size and the number of detected particles depending on different causes of failure.
Figure 5B:
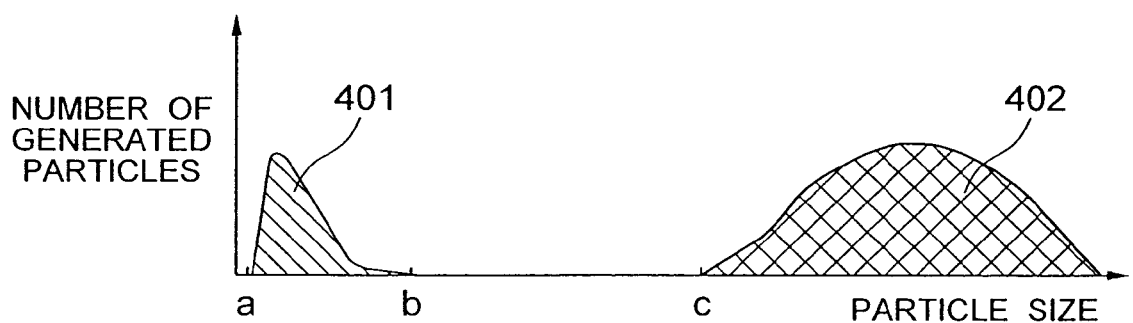
Figure 5C:
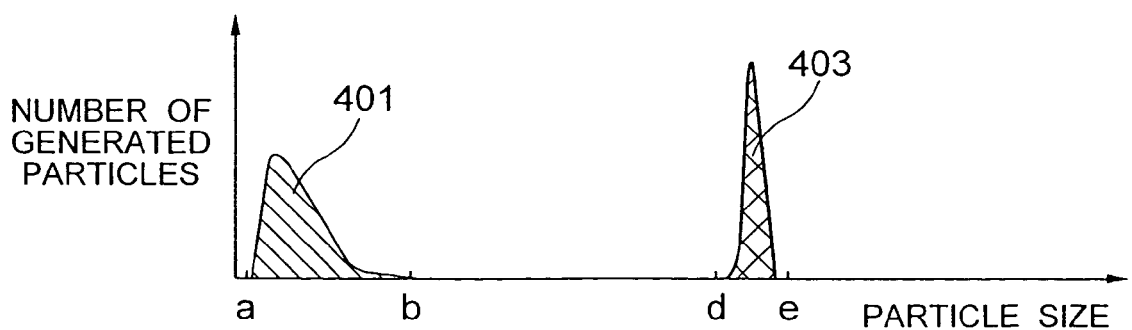

FIGS. 5A to 5C are diagrams showing that the relationship between particle sizes and the number of detected particles changes due to a cause of failure.

Figure 6:
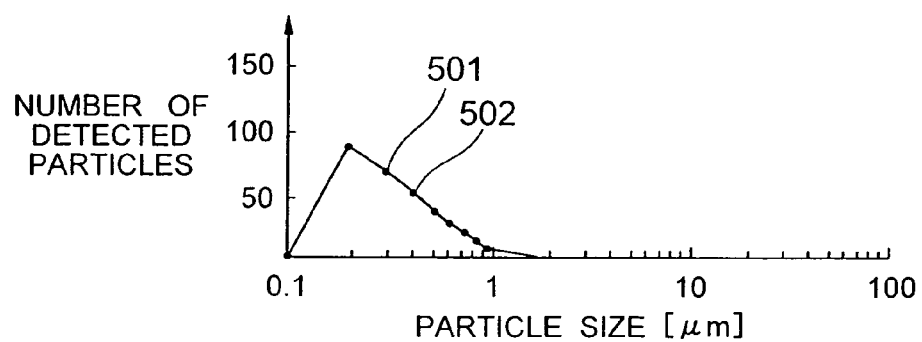
FIG. 6 is a graph showing the relationship between the number of detected particles and the particle size.

FIG. 6 is a line graph showing the number of detected particles and particle sizes.

Figure 7:
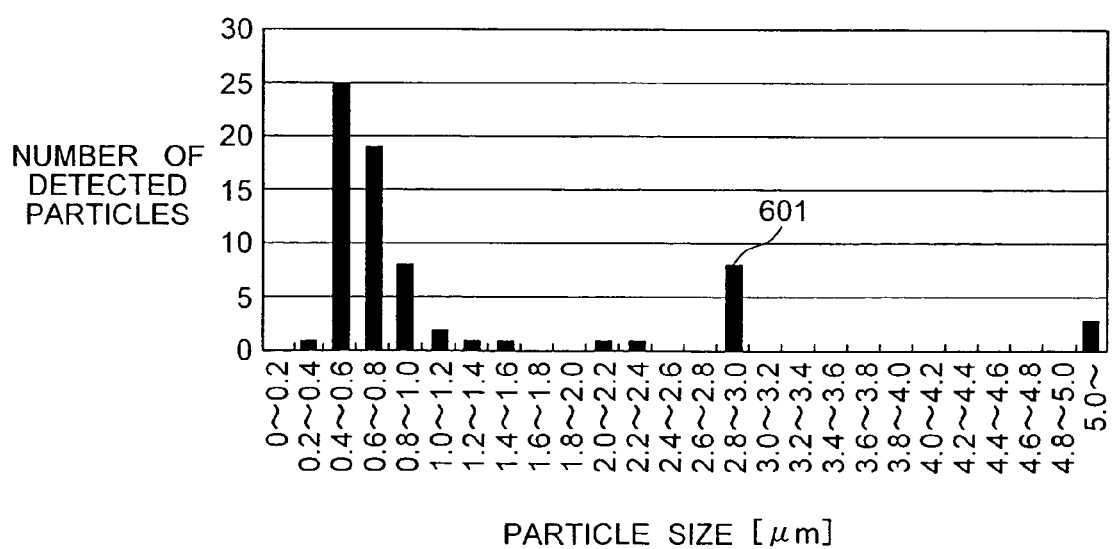
FIG. 7 is a histogram showing the relationship between the number of detected particles and the particle size.

FIG. 7 is a histogram showing the number of detected particles and particle sizes.

Figure 8A:
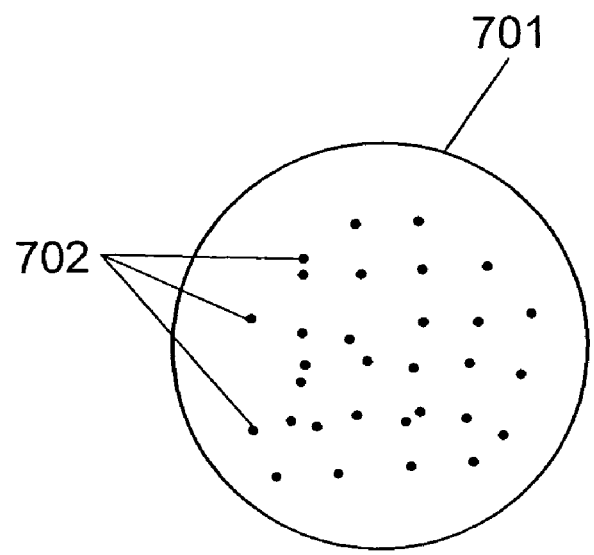
FIGS. 8A and 8B are diagrams clearly illustrating particles of a particular size on a wafer.
Figure 8B:
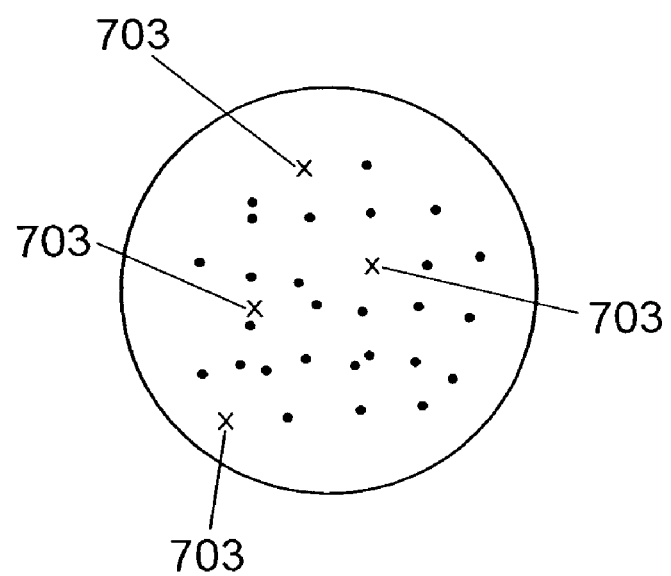
Figure 9A:
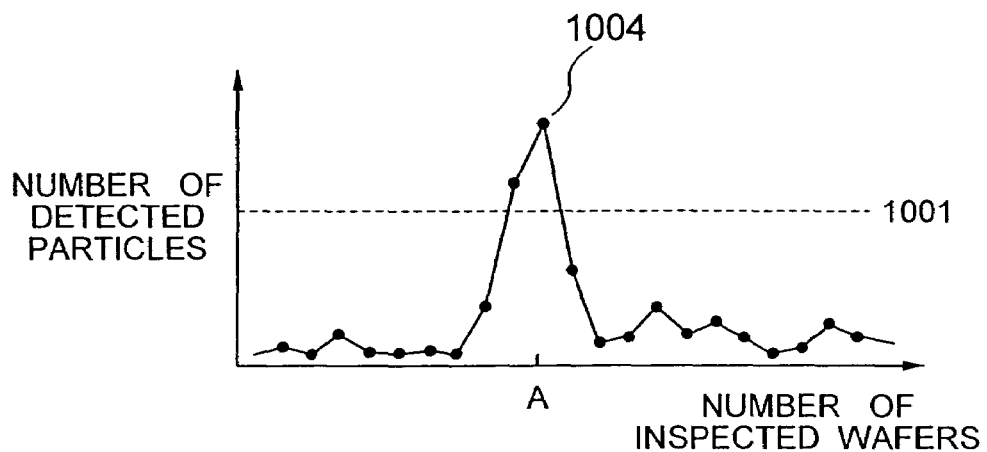
FIGS. 9A to 9C are graphs each showing in time series a transition of the number of detected particles having a particular size.
Figure 9B:
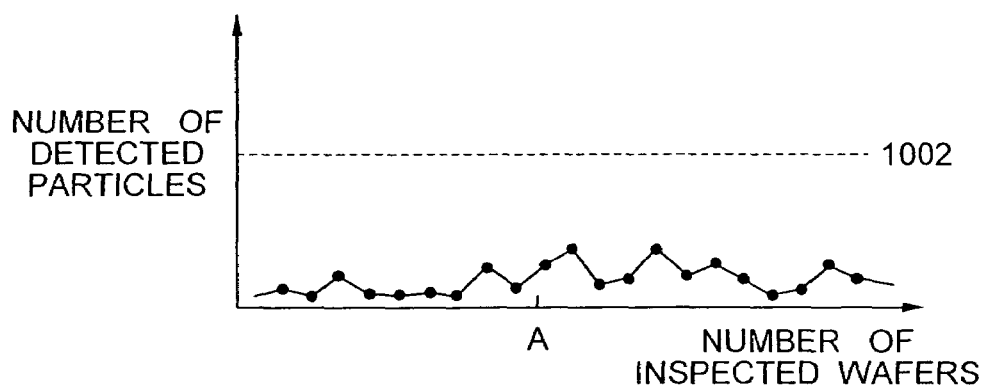
Figure 9C:
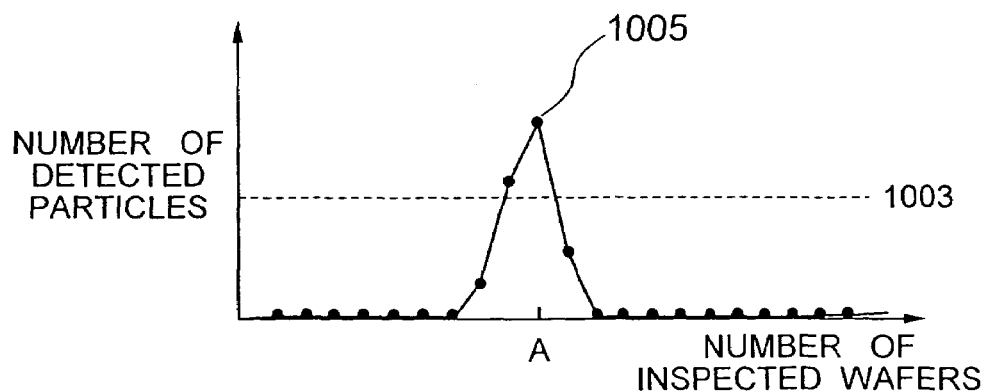

FIGS. 8A, 8B are schematic diagrams each clearly showing particles of a particular size on a wafer;

FIGS. 9A to 9C are graphs each showing a transition of the number of detected particles for each particular size.

Figure 10:
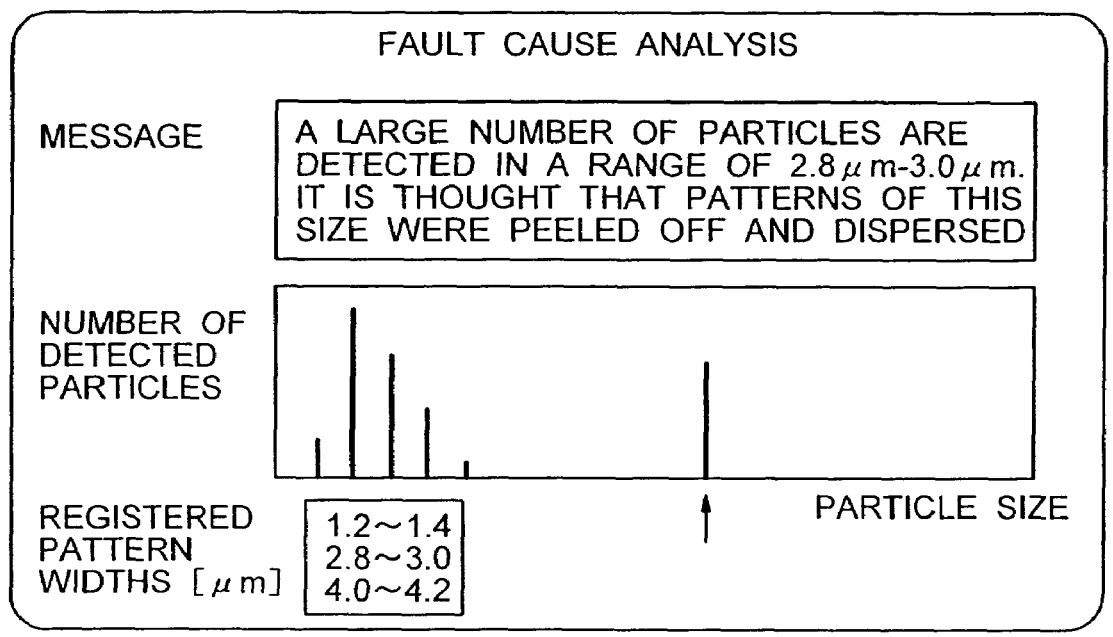
FIG. 10 is a front view of a screen which displays for the user a cause of failure which results in the generation of particles.

FIG. 10 is a diagram illustrating a screen for displaying to the user a cause by which particles are generated.

Figure 20:
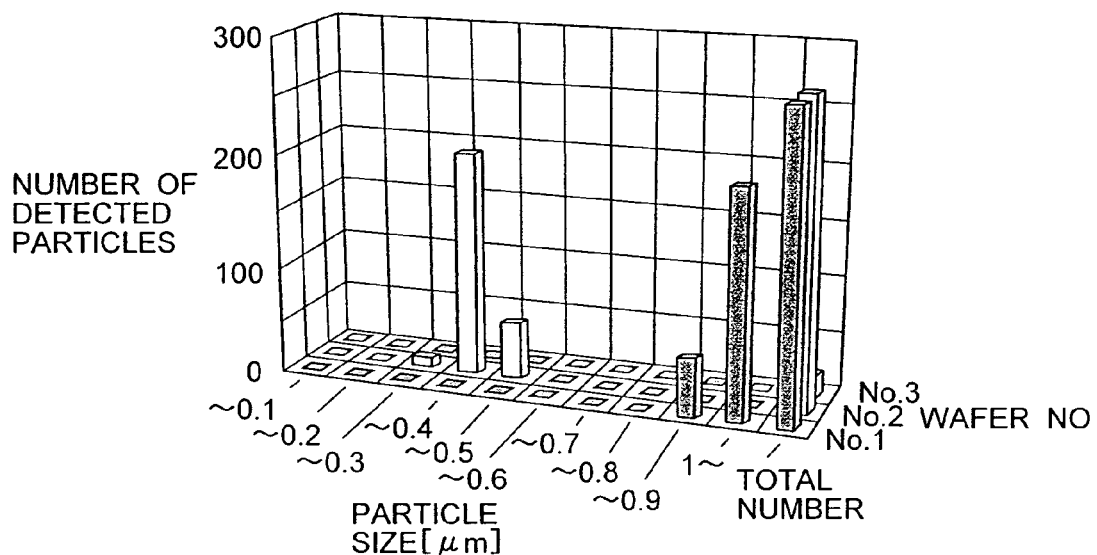
FIG. 20 is a histogram showing the relationship between the number of detected particles and the particle size for a plurality of objects under inspection.

FIG. 20 is a histogram showing the number of detected particles and the particle sizes on a plurality of wafers.

Figure 21:
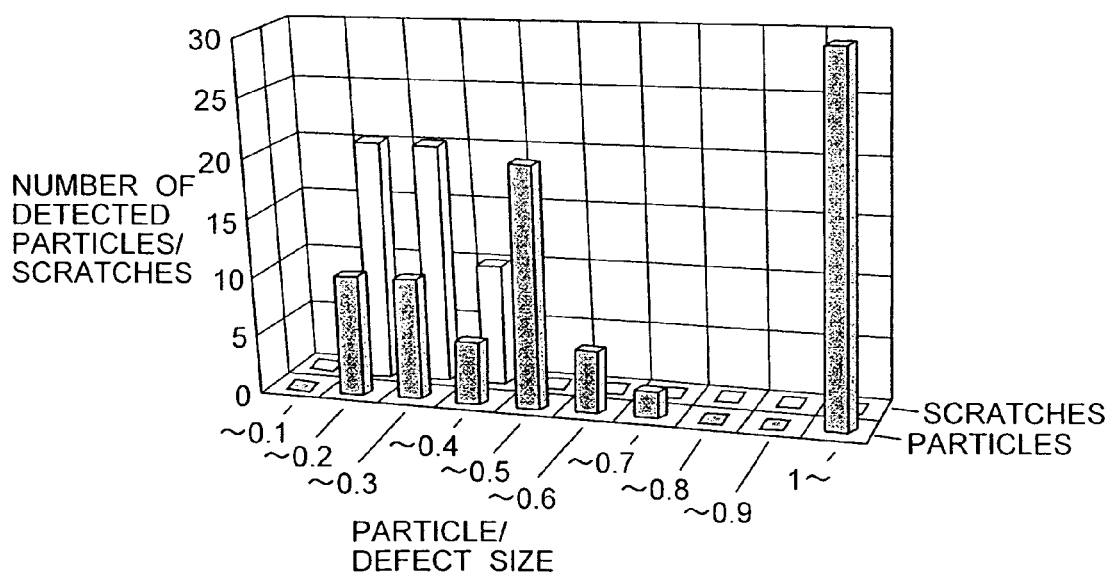
FIG. 21 is a histogram showing the relationship between the number of detected particles/scratches and the particle/scratch size separately for particles and scratches.

FIG. 21 is another histogram separately showing detected particles and scratches on a wafer.

One important idea of the present invention is to use particle size information for analyzing a cause of failure. The following description will be made on the effectiveness of using the particle size information for analyzing a cause of failure.

Assume herein that particles have been detected from a wafer processed by a semiconductor manufacturing apparatus, for example, an etching apparatus, and the relationship between particle sizes and the number of detected particles are as shown in FIGS. 5A to 5C. A region 401 in FIG. 5A shows a distribution of particles steadily generated in a process of an etching apparatus. In this case, the particle sizes concentrate in a range from a to b, so that a gently-sloping mountain is formed.

On the other hand, FIG. 5B shows an exemplary distribution of particles which are generated when the apparatus is faulty. In this case, large particles (a range of sizes larger than c) are frequently generated as shown in a region 402, in addition to the particles in the steady state shown in the region 401. It is contemplated that the cause for such large particles is deposits on the inner wall surface of the etching apparatus are peeled off the wall surface during the etching process. FIG. 5C also shows an exemplary distribution of particles which are generated when a failure occurs. In this case, FIG. 5C shows that particle sizes also concentrate in a range from d to e in addition to the particles in the steady state. It is contemplated that the cause for such particles is particular patterns which are peeled off and dispersed during the etching process.

As described above, in manufacturing apparatuses for semiconductor or the like, there is a relationship between the sizes of generated particles and the cause by which the particles are generated, so that the cause for particles generated in a certain manufacturing apparatus can be immediately known by managing the generation of particles of particular sizes. In other words, by investigating the relationship between the size of particles and the number of generated particles, the cause of failure can be revealed.

It should be understood that the values a–e of course depend on particular manufacturing apparatuses, manufacturing processes and so on. Also, particles generated by a different cause may exhibit a different distribution of size, so that it is preferred to prepare data which conforms to a particle size distribution for each cause. In addition, while this embodiment intends to identify the cause for generated particles in two ranges, the range of particle size may be divided into more than two ranges.

Next, description will be made on a specific function of analyzing a cause of failure.

First described is how the particle sizes and the number of detected particles are displayed on the data display unit 106. The data display unit 106 displays a graph showing a particle size distribution as described above, i.e., a graph which allows the user to understand the relationship between particle sizes and the number of detected particles. FIG. 6 is a graph showing the particle size on the horizontal axis and the number of detected particles on the vertical axis. A point 501 indicates the number of detected particles of certain size. In this exemplary graph, data on the number of detected particles is provided in increments of 0.1 $\mu$m. A curve 502 is a line connecting the points 501. By displaying the graph as in this embodiment, it can be immediately seen how particles detected from an object under inspection 102 are distributed.

In the graph of FIG. 6, a minimum value on the horizontal axis may be a minimal detectable dimension of the particle inspection apparatus, or a particle size which should be managed on a semiconductor manufacturing line. Also, the scale may be represented in a logarithmic or linear form. The unit of scale may be variable. Further, a displayed range of each axis may be fixed or variable. For example, particles generated by a particular cause alone may be displayed by displaying particles of a particular size. The contents represented on the vertical axis and the horizontal axis may be replaced with each other. Instead of the number of detected particles, the density of particles may be shown. Further, while this embodiment displays a graph, an average value of the graph, and a standard deviation or variance of the graph may also be displayed other than the graph.

Also, while this embodiment displays particle data on one wafer as one graph, the graph need not be displayed for only one wafer. An average value, a standard deviation and a variance of particle data on a plurality of wafers may be displayed, and particle data on a plurality of wafers may be displayed side by side.

Figure 32:
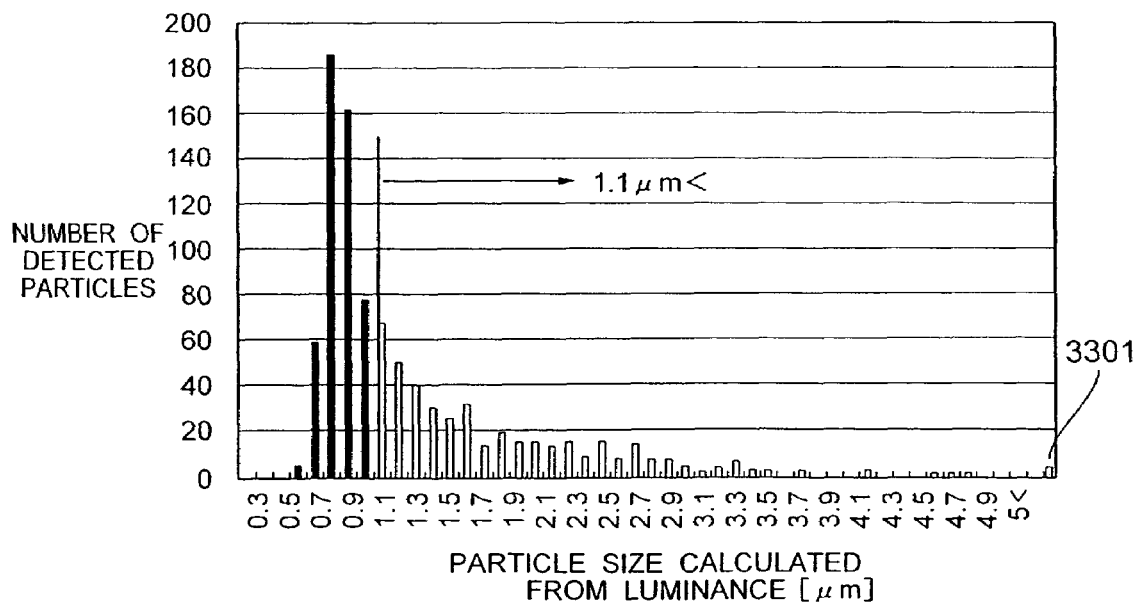
FIG. 32 is a histogram showing the relationship between particle sizes and the number of the particles measured by the apparatus for inspecting particles or defects according to the present invention.

The graph may be displayed in histogram as shown in FIGS. 7 and 32. The graphs on these figures indicate the particle size on the horizontal axis, and the number of detected particles on the vertical axis, similarly to FIG. 6. These graphs display the particle size on the horizontal line divided into certain sections. FIG. 7 shows data sections in increments of 0.2 $\mu$m. FIG. 32 in turn shows data sections in increments of 0.1 $\mu$m, wherein particles having the size equal to or more than 5 $\mu$m are counted in a bar graph 3301, and a histogram for particles having the size smaller than 1.1 $\mu$m and a histogram for particles having the size equal to or larger than 1.1 $\mu$m are displayed in different colors, by way of example. In addition, a function may be added for displaying information on the positions of a detected particles in a selected portion of a bar graph. Also, a review image may be displayed for the detected particles in the selected portion.

Figure 34:
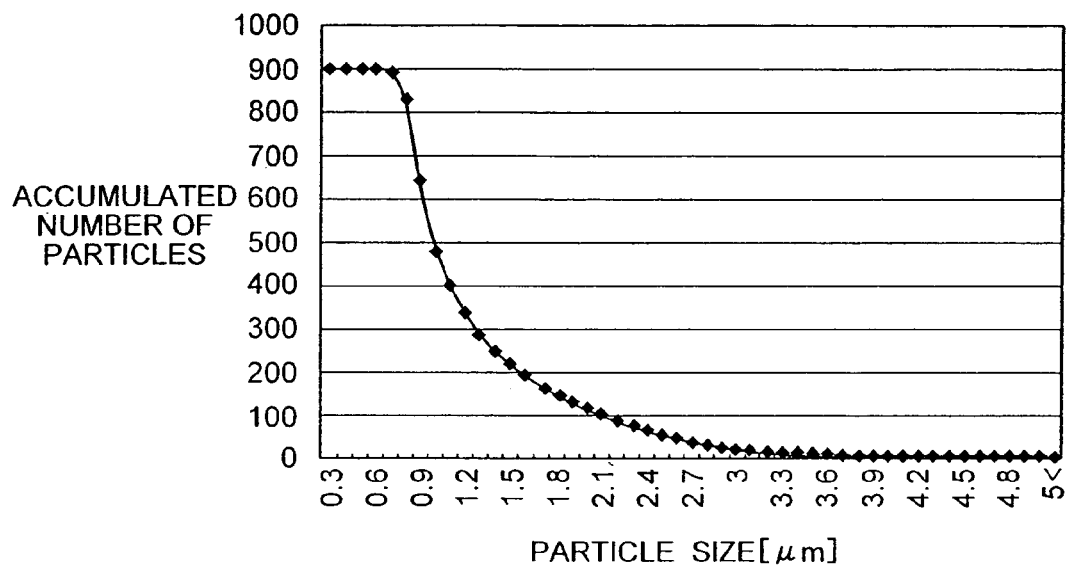
FIG. 34 is a graph showing an exemplary display of the accumulated number of particles by size, using the apparatus of inspecting particles or defects according to the present invention.

FIG. 34 shows another example of graphical representation. FIG. 34 shows an example in which the particle size is set on the horizontal axis, and an accumulated number of particles is set on the vertical axis. Here, the accumulated number refers to the number of detected particles of a certain size or larger.

Figure 35:
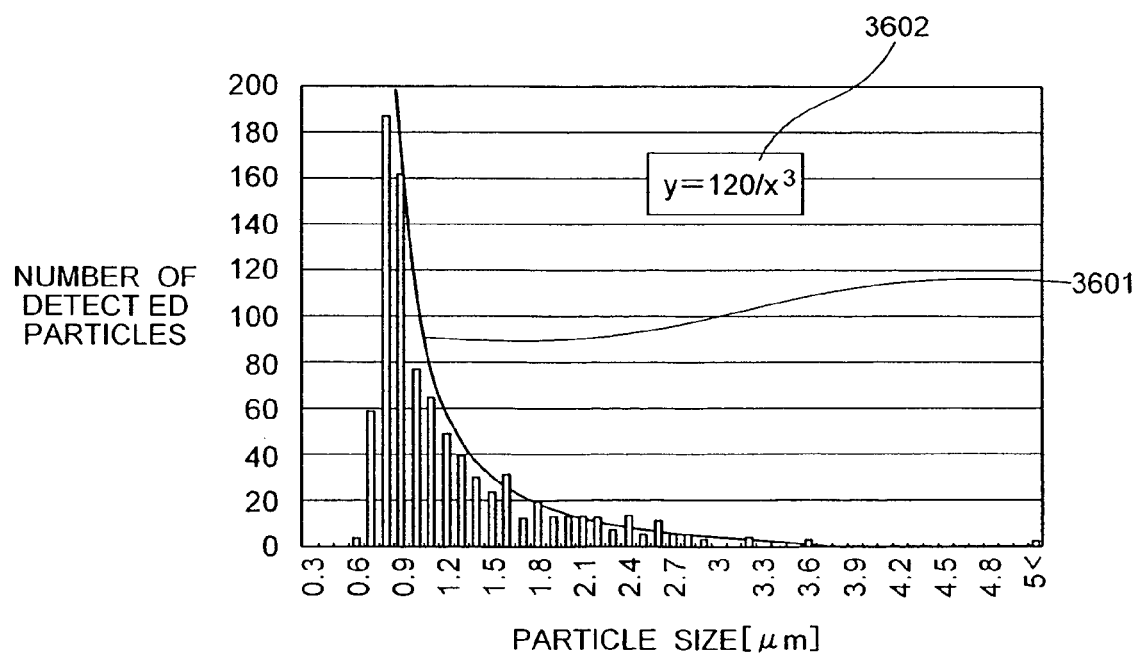
FIG. 35 is a graph showing the relationship between particle sizes and the number of the particles measured by the apparatus for inspecting particles or defects according to the present invention, together with a distribution of the detected particles.

FIG. 35 shows a further example of graphical representation. FIG. 35 shows an example in which the particle size is set on the horizontal axis, and the number of detected particles is set on the vertical axis, with a curve 3601 indicative of the number of detected particles, and an equation expressing the curve 3601 indicative of the number of detected particles additionally indicated in the graph. In the equation 3601, x represents the particle size, and y the number of detected particles. The equation 3601 is an approximate equation derived from the number of detected particles for each particle size. The curve 3601 represents the equation 3602.

FIG. 20 shows a further example of graphical representation. While the example in FIG. 7 displays data for one wafer, data on a plurality of wafers may be displayed side by side as shown in FIG. 20. Specifically, FIG. 20 is an example in which the number of detected particle is set on one of three coordinate axes; the particle size on another axis; and the wafer number on the remaining axis. In this example, data sections for the particle size are set in increments of 0.1 $\mu$m from zero to 1 $\mu$m, particles having sizes equal to or larger than 1 $\mu$m are counted on the same bar graph, and the total number of detected particles is also displayed in the graph. As is the case with FIG. 6, an average value, standard deviation and variance may also be displayed on the graph of FIG. 20.

FIG. 21 shows a further example of graphic representation. FIG. 21 shows an example in which displayed data are classified into particles and scratches and also classified by size.

Next, description will be made on a function of displaying information on the positions of detected particles. FIG. 8A shows information on the positions of all particles detected by a particle inspection.

In FIG. 8A, detected particles 702 exist within a contour 701 of an 8-inch semiconductor wafer. In this event, as a mouse is click once or twice on a bar graph 601 in FIG. 7, the section of the bar graph 601, i.e., displayed particles 703 of sizes ranging from 2.8 $\mu$m to 3.0 $\mu$m in FIG. 8A are changed as shown in FIG. 8B. The inspection apparatus has such a function so that the user can immediately find the positions on an object under inspection 102 of particles having sizes in a particular range.

Figure 22:
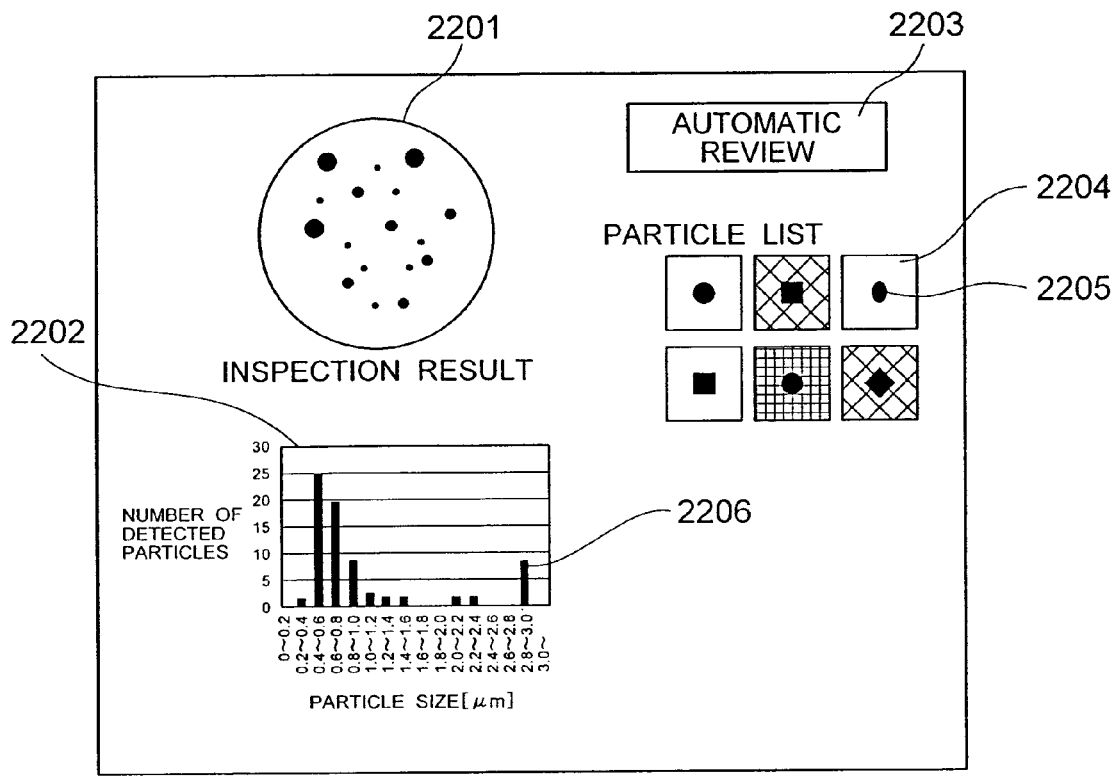
FIG. 22 is a front view of a display showing a method of displaying detected particles of particular sizes in the apparatus for inspecting particles or defects according to the present invention.

FIG. 22 shows an exemplary result of a particle inspection displayed after the inspection. The display in FIG. 22 comprises an inspection map 2201 indicative of the positions at which particles are detected; a histogram 2202 for the sizes of the detected particles; a review button 203; a review image 2204 of the detected particles; particles 2205; a particle size data section 2206 to be reviewed. The review image 2204 is displayed centered at the particle 2205. In this example, particles having sizes ranging from 2.8 $\mu$m to 3.0 $\mu$m in the data section 2206 are selected.

In operation, after particles are inspected by the apparatus for inspecting particles or defects according to the present invention, the inspection map 2201 is displayed as information on the positions of the particles, and the histogram 2202 is displayed as information on particle sizes. Then, the data section 2206 is selected as a particle size to be reviewed. Clicking on the review button 2203 causes the review image 2204, provided by the apparatus for inspecting particles or defects of the present invention, to be displayed. Here, the review image 2204 may be an image generated from scattered laser light, or an image captured by a microscope.

Next, a management approach applied when the statistics are collected in time series on particles having a particular size will be described with reference to FIGS. 9A to 9C.

FIG. 9A shows a transition of the total sum of all particles, irrespective of the size, detected by the particle inspection apparatus, in time series for wafers processed in the same process by the same manufacturing apparatus. FIG. 9C shows a transition of the total sum of particles having sizes ranging from 2.8 to 3.0 [$\mu$m], shown in the example of FIG. 7, in time series. FIG. 9B shows a transition of the total sum of the remaining particles in time series.

Thresholds 1001, 1002, 1003 indicate management reference values for the number of particles in the three cases. When particles exceeding these thresholds are detected, this means that an associated wafer is diagnosed as defective. Specifically, it is determined from FIG. 9A that a peak value 1004 near an inspection time A is unusually high.

However, while a certain failure may be guessed from the statistics shown in FIG. 9A, its cause cannot be revealed.

On the other hand, when particles are managed by size in accordance with the inspection approach of the present invention, a remarkable peak 1005 appears at A time in FIG. 9C, so that it is understood that particles having sizes ranging from 2.8 to 3.0 [$\mu$m] particularly concentrate in a lot which was inspected at that time. Thus, from the fact that no section exceeds the threshold in FIG. 9B and the peak value 1005 is sensed in FIG. 9C, the user can guess by the reason shown in FIGS. 5A to 5C that patterns of these sizes peeled off and scattered on wafers during an etching process can be the cause for an unusual increase in the number of particles, and therefore immediately take effective countermeasures to the failure, such as checking the etching apparatus.

Next, an example of displaying a cause of failure to the user will be described with reference to FIG. 11.

The apparatus for inspecting particles or defects according to the present invention has a function of analyzing the particle size and the number of detected particles to display a cause of failure to the user.

For example, assume that a graph as shown in FIG. 7 results from an inspection, taking the cause of failure shown in FIG. 5C as a model. Assume also that a section d–e in FIG. 5C corresponds to the particle size range of 2.8 $\mu$m to 3.0 $\mu$m in FIG. 7. Therefore, when the result of inspection shown in FIG. 7 is obtained, the screen shown in FIG. 9 is displayed to clarify the user the result of analysis on the cause of failure.

Next described is another exemplary management approach based on the particle size. Particles detected by the inspection apparatus may be classified into those which cause a failure, and those which do not cause a failure. Specifically, if particles are smaller than wire widths and spaces between wires in a wiring pattern created on a wafer, such particles cause no failure in many cases. Therefore, detected particles having a certain size or more may be managed as a possible cause of failure.

Figure 23:
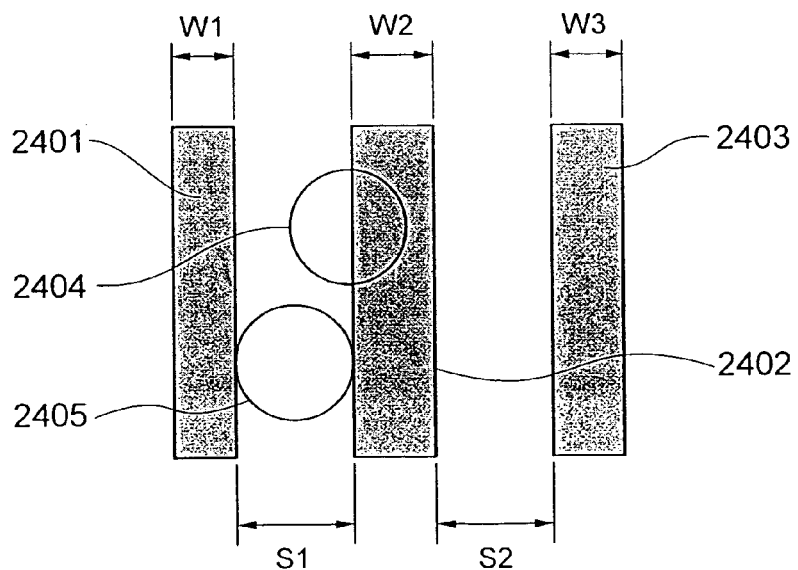
FIG. 23 is a plan view of a wiring pattern for explaining the relationship between the wiring pattern and a particle size.

Next, description will be made on an exemplary method of calculating a particle size to be managed. FIG. 23 shows the relationship between a wiring pattern 2401 having a wire width W1, a wiring pattern 2402 having a wire width W2 and a wiring pattern having a wire width W3 on a wafer, and a particle 2404. When this particle 2404 is conductive, the particle 2404 attached, for example, at a position 2405 to connect the wiring pattern 2401 and wiring pattern 2402 would cause the wiring pattern 2401 and wiring pattern 2402 to short-circuit through the particle 2404, with the result that this chip becomes defective. As such, assuming that the distance between the wiring pattern 2401 and wiring pattern 2402 is S1, and the distance between the wiring pattern 2402 and wiring pattern 2403 is S2, the particle 2404 which can short-circuit the wiring pattern 2402 to another wire has a size of S1 or S2 or more. Particularly, a particle having a size of (S1+W2+S2) will short-circuit wires with possibility of 100%.

Therefore, when the wiring patterns have the widths and distance between wires as defined above, the size of a particle causing a failure is given by: MIN (S1, S2) where MIN (A, B) indicates the smaller value of A and B when they are compared.

It should be noted that the example shown herein is a calculation for the most strict condition in management. If the condition is less strict, larger particles may be managed.

By determining a particle size to be managed in each manufacturing process by the calculation described above and monitoring fluctuations in the number of detected particles having the managed size or more, it is possible to sense the occurrence of a failure without delay. A monitoring method used herein may involve previously calculating an average and standard deviation of the number of particles under management detected, for example, from several to several tens of wafers, monitoring the number of particles based on a monitoring threshold calculated by:

Monitoring Threshold=Average+$k$·Standard

Deviation and analyzing a cause of failure and taking countermeasures to wafers on which the number of detected particles exceeds the monitoring threshold. In the above equation, k is a constant which may be set to k=3, for example, when it is desired that the failure analysis is conducted for approximately 0.3% of all wafers.

Next described is another method of calculating a particle size to be managed. This method calculates the influence of particles exerted on the yield of wafers from the presence or absence of particles detected on one wafer, and determination made to chips on which the particles are detected as to whether they are non-defective or defective, and manages a particle size at which the calculated influence present a maximum.

Figure 29:
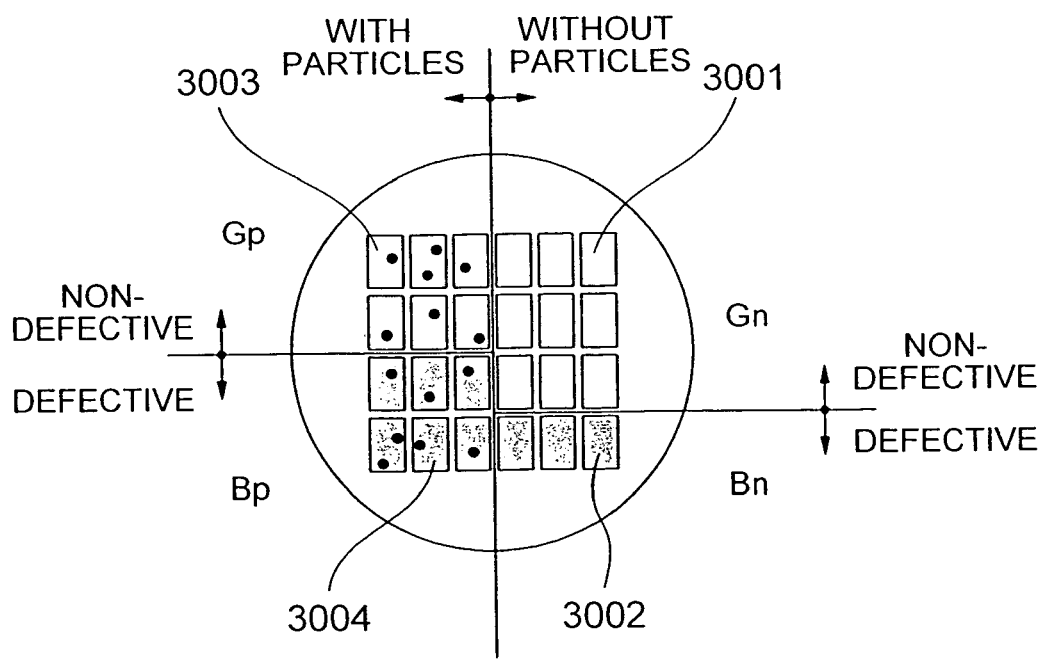
FIG. 29 is a plan view of a wafer for explaining a method of calculating the influence on the yield from the presence or absence of particles.

A method of calculating the influence on the yield will be described with reference to FIG. 29. FIG. 29 shows chips on a wafer classified according to the presence or absence of particles, and non-defective and defective chips. Specifically, FIG. 29 shows chips 3001 (hereinafter labeled "Gn") on which no particles have been detected and which are non-defective; chips 3002 (hereinafter labeled "Bn") on which no particles have been detected but which are defective; chips 3003 (hereinafter labeled "Gp") on which particles have been detected but which are non-defective; and chips 3004 (hereinafter labeled "Bp") on which particles have been detected and which are defective. Here, whether or not particles have been detected on a certain chip may be determined based on the position information in the result of an inspection performed by the apparatus for inspecting particles or defects according to the present invention. Also, determination as to whether a certain chip is non-defective or defective may be made using, for example, the result of an electric inspection.

First, assuming that the yield of a certain wafer is Y, and the yield of chips on which no particles have been detected is Yn, the influence dY of detected particles on the yield of the wafer is defined as:

$dY=Yn-Y$

Since Y is the yield of the wafer, Y can be expressed by:

$Y=Yn \cdot (1-\gamma)+Yp \cdot \gamma$ where Yp is the yield of chips on which particles have been detected, and γ is the proportion of chips on which particles have been detected with respect to the total number of chips (hereinafter called the "particle occurrence frequency").

Here, using the aforementioned Gn, Bn, Gp, Bp:

$Y=(Gn+Gp)/(Gn+Bn+Gp+Bp)$ $Yn=Gn/(Gn+Bn)$ $Yp=Gp/(Gp+Bp)$ $\gamma=(Gp+Bp)/(Gn+Bn+Gp+Bp)$ can be derived.

Therefore, dY can be expressed as follows:

$$\begin{aligned} dY &= Yn - Y \\ &= Yn - (Yn \cdot (1-\gamma) + Yp \cdot \gamma) \\ &= (Yn - Yp) \cdot \gamma \\ &= Yn \cdot (1 - Yp/Yn) \cdot \gamma \end{aligned}$$

Here, assuming that the probability of a chip determined as defective due to particles is represented by F (hereinafter called the "critical probability"), Yp can be expressed by:

$Yp=Yn \cdot (1-F)$

Rewriting the above equation for F, $F=1-Yp/Yn$ so that dY can be expressed by:

$dY=Yn \cdot F \cdot \gamma$

Here, the particle occurrence frequency γ is larger as a particle detection sensitivity is higher, and smaller as the particle detection sensitivity is lower. This is because a higher detection sensitivity contributes to detection of a larger number of particles. The critical probability F in turn is smaller as the particle detection sensitivity is higher, and larger as the particle detection sensitivity is lower. This is because although a higher sensitivity contributes to detection of smaller particles, those particles which are smaller than the distance between wiring patterns do not cause a failure such as short-circuiting.

Therefore, when the influence dY on the yield is calculated, the particle sizes used in the calculation are limited. The particle size which maximizes the influence dY on the yield indicates the minimum particle size to be managed. The limitation on the particle sizes refers to using those data on particles having a certain size or more.

Figure 24:
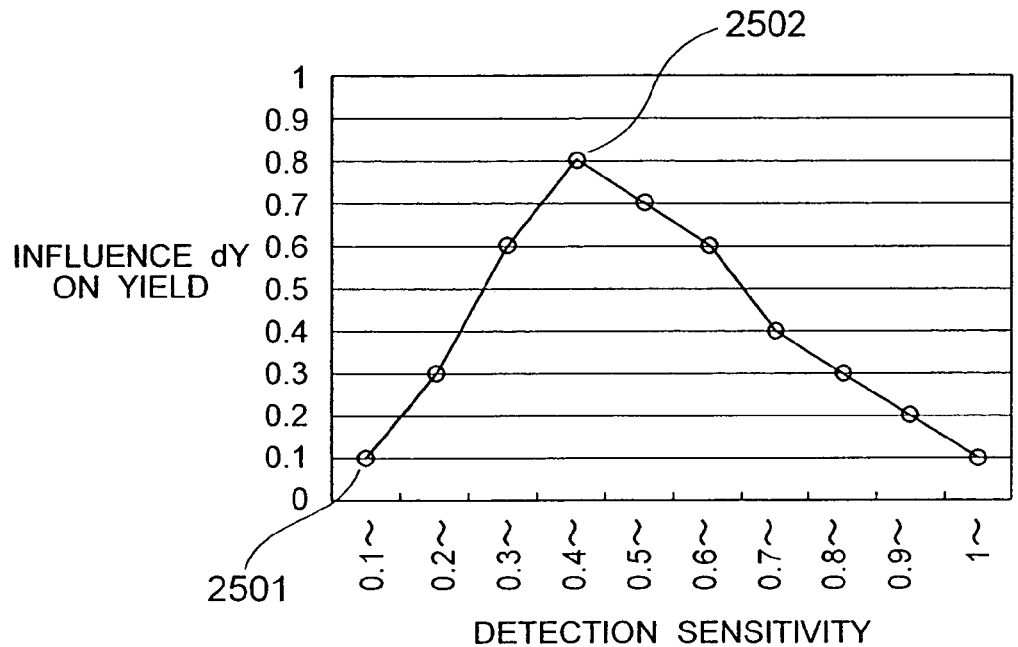
FIG. 24 is a graph showing the relationship between a detection sensitivity and the influence of particles on a yield, when the apparatus for inspecting particles or defects according to the present invention is used.

FIG. 24 shows an exemplary result of calculating the influence dY on the yield. FIG. 24 shows the influence dY on the yield on the vertical axis, and the particle size used in calculating the influence dY on the yield on the horizontal axis. For example, in FIG. 24, a point 2501 indicates that the influence dY on the yield is 0.1 as a result of the calculation using data on particles having sizes equal to or more than 0.1 μm, and a point 2502 indicates that the influence dY on the yield is 0.8 as a result of the calculation using data on particles having sizes equal to or more than 0.4 μm. Here, using data on particles having the sizes equal to or more than 0.1 μm means that the calculation is performed on the assumption that among detected particles, chips on which particles of 0.1 μm or more have been detected are regarded as chips on which particles are attached, and chips on which particles less than 0.1 μm have been detected or no particles have been detected are regarded as chips on which no particles are attached. Thus, it is appreciated from FIG. 24 that the influence dY on the yield is the largest when it is calculated using data on particles of 0.4 μm or more, so that particles of 0.4 μm or more should be managed.

While the foregoing embodiment shows that the particle size is changed in increments of 0.1 μm, the increment may be 0.2 μm or any other value. Also, while the foregoing embodiment has been described for an example which determines the particle size that exerts the largest influence dY on the yield as the method of determining a particle size to be managed, the particle size to be managed need not be the particle size that exerts the largest influence, but may be a particle size that presents a value close to the largest influence dY on the yield, for example, a value equal to or more than the largest influence dY multiplied by 0.9.

Figure 33A:
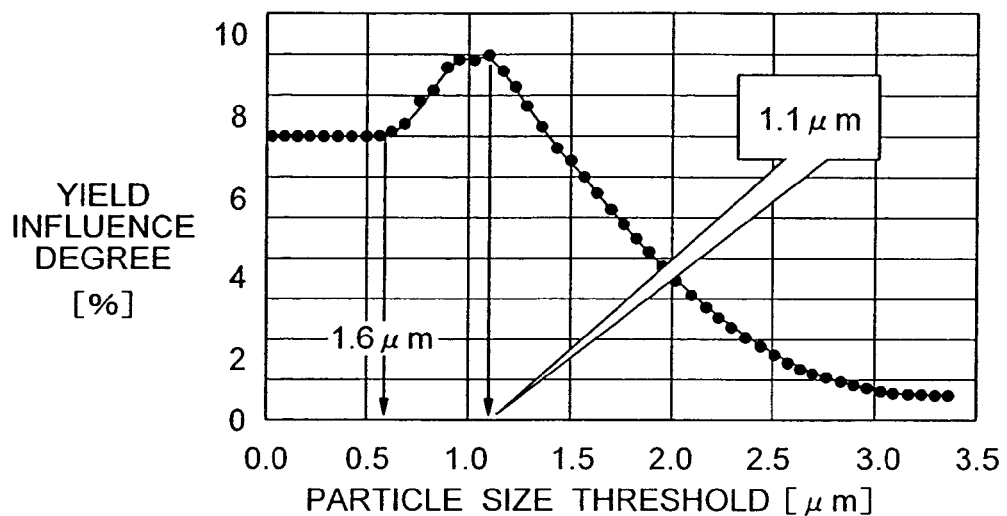
FIG. 33A is a graph showing the relationship between particle sizes measured by the apparatus for inspecting particles or defects according to the present invention, and the yield.
Figure 33B:
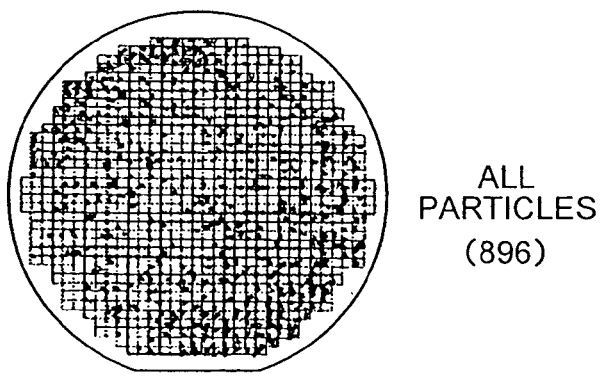
FIGS. 33B and 33C are plan views of wafers each showing a distribution of detected particles on the wafer.
Figure 33C:
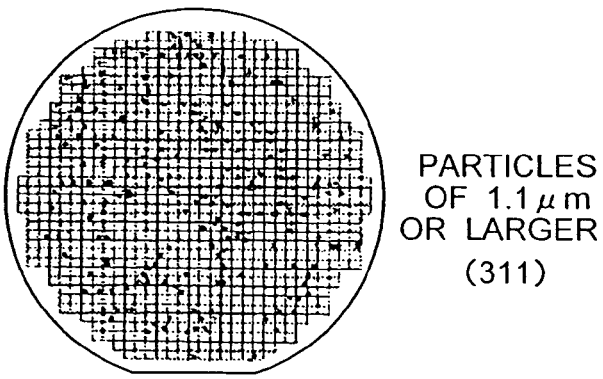

FIGS. 33A to 33C show another exemplary result of calculation. FIGS. 33A to 33C show the result of calculating the influence dY on the yield; and particle detection maps at that time. FIG. 33A shows, by way of example, that the influence dY on the yield is calculated in increments of approximately 0.07 μm of particle size, and values on the vertical axis are represented in percent. FIG. 33B is a particle detection map which displays all particles detected by the apparatus for inspecting particles or defects according to the present invention, and FIG. 33C is a particle detection map which shows extracted particles having the sizes equal to or more than 1.1 μm. The value of 1.1 μm indicates the particle size that exerts the largest influence dY on the yield in FIG. 33A. It is therefore understood that particles may be managed based on the particle detection map of FIG. 33C.

Figure 25:
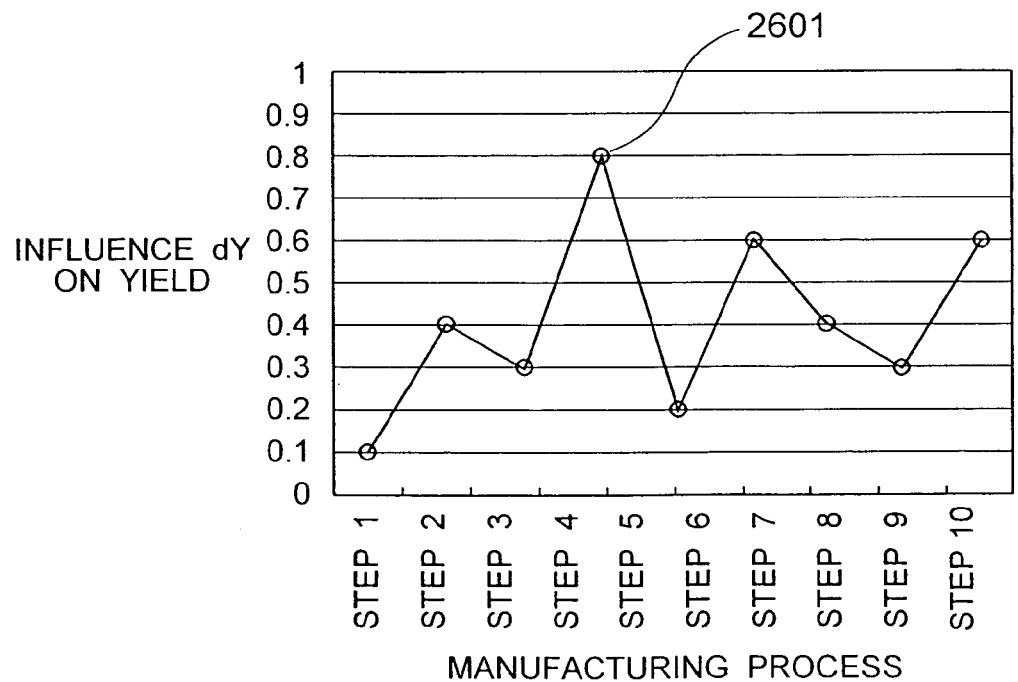
FIG. 25 is a graph showing an example of calculating the influence on the yield for each manufacturing step.

Next, description will be made on an approach for managing a semiconductor device manufacturing process when the influence dY on the yield is used for the management. FIG. 25 shows a graph which sets the aforementioned influence dY on the yield on the vertical axis, and a semiconductor manufacturing process on the horizontal axis. Specifically, the horizontal axis shows steps in the process in which particles are inspected using the apparatus for inspecting particles or defects according to the present invention.

Next, the operation will be described. First, an inspection is conducted in each of the steps in the process shown on the horizontal axis using the same wafer. Next, at the time each of chips on the wafer is determined as non-defective or defective, the aforementioned influence dY on the yield is calculated for each step. FIG. 25 is an example of calculating the influence dY on the yield in each step. For example, a point 2601 indicates that the influence dY on the yield is 0.8 when calculated using particles detected in a step labeled "Step 4" in the process. In this way, the influence dY on the yield is calculated in each step, and countermeasures are taken preferentially from a step which presents a larger influence dY on the yield, thereby making it possible to take countermeasures from a step which is more likely to cause a failure.

In the foregoing embodiment, all data on particles detected in each step are used for calculating the influence dY. For particles which have been known that they had occurred in a different step, the influence dY on the yield may be calculated using the remaining data except for the data on the particles. For removing data, for example, information on the position of particles detected in Step 1 in FIG. 25 may be compared with information on the position of particles detected in Step 2, and the particles previously detected in Step 1 may be deleted from data on particles in Step 2.

Also, the foregoing embodiment has been described for the management of particle size using the influence dY on the yield expressed by:

$$dY = Yn \cdot F \cdot \gamma$$

When a failure caused by a process is eliminated by improving the process management, $$dY = F \cdot \gamma$$

may be used by setting the aforementioned Yn to one (Yn=1). The approach of the present invention may also be applied to any index for calculating the influence of particles. For example, for memory products such as DRAM, the number of defective bits caused by each particle may be used as an index.

The foregoing embodiment is advantageous in that since wiring pattern widths and space widths in a semiconductor device are only required as information for determining whether a particle causes a failure in the example described with reference to FIG. 23, a particle size to be managed can be determined at the time the design of a semiconductor device is definite. The example described with reference to FIG. 29, in turn, is advantageous in that it employs an index including a consideration of information such as short-circuiting of wires due to the height of a particle, and so on, as well as the width of the particle, so that the actual state of device can be known.

[Inspection on Particles by Region and Analysis on Cause of Failure]

Next, description will be made on an embodiment which manages particle data by region on a wafer to take countermeasures using the apparatus for inspecting particles or defects according to the present invention.

Figure 11:
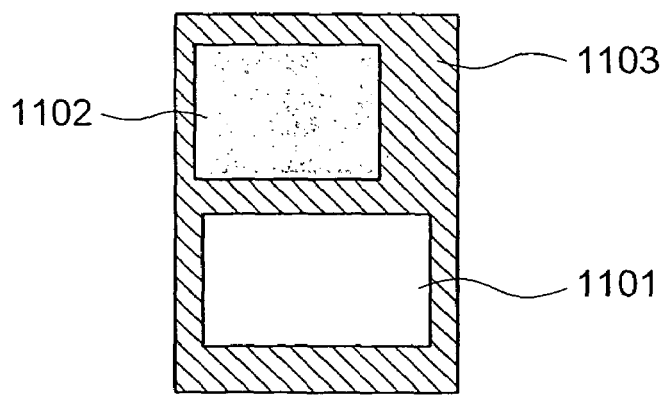
FIG. 11 is a plan view schematically illustrating regions on a semiconductor wafer.

FIG. 11 schematically illustrates regions on a semiconductor wafer.

Figure 12A:
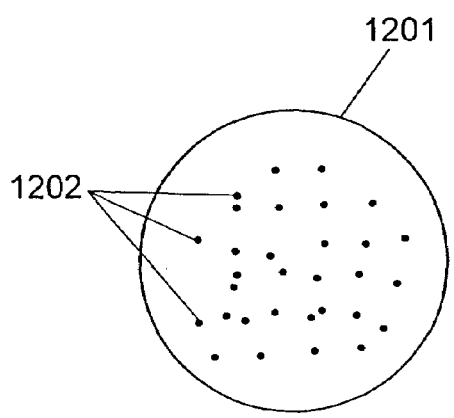
FIGS. 12A and 12B are plan views each clearly showing particles of a particular size on a wafer when particle data is managed separately for each region.
Figure 12B:
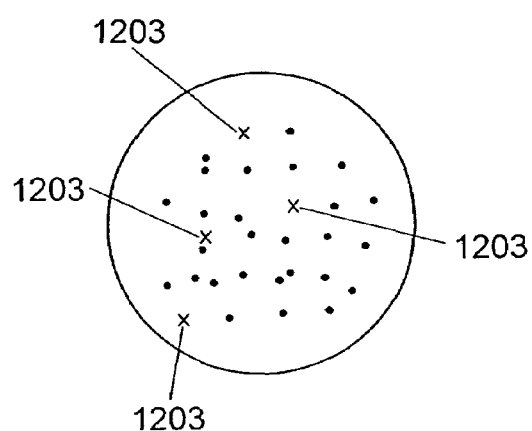
Figure 13:
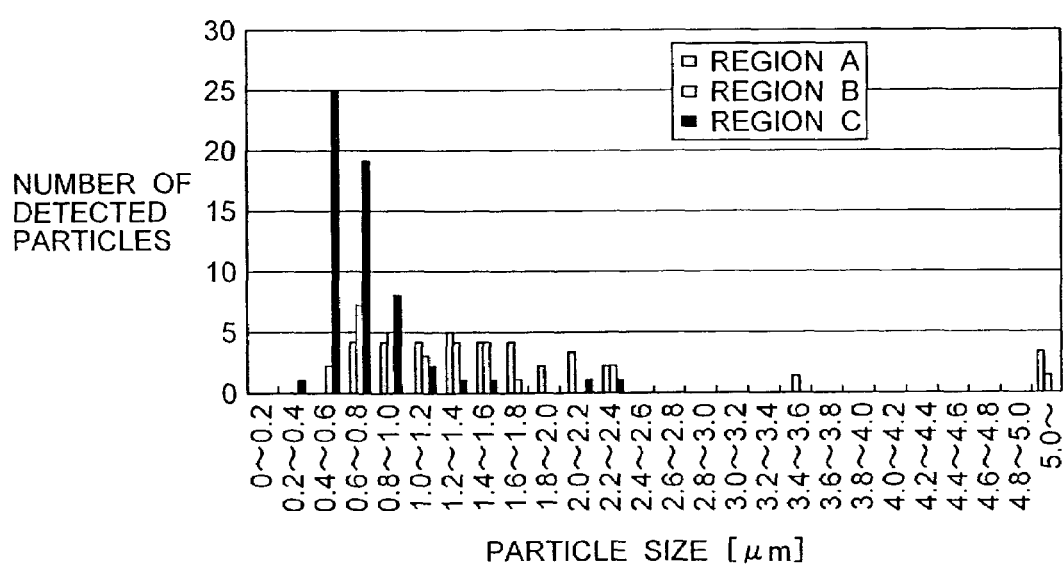
FIG. 13 is a graph (No. 1) showing the relationship between the particle size and the number of detected particles in each of regions.
Figure 14:
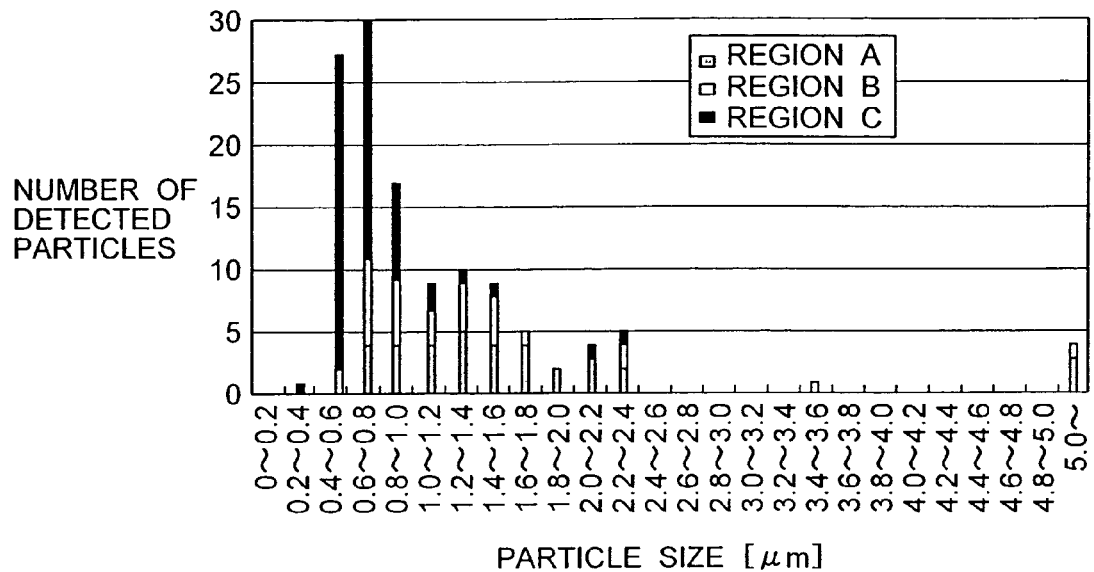
FIG. 14 is a graph (No. 2) showing the relationship between the particle size and the number of detected particles in each of regions.

FIGS. 12A, 12B are schematic diagrams each clearly showing particles of a particular size on a wafer when particle data is managed separately for each region;

FIGS. 13, 14 are graphs each showing the number of detected particles by size in each region.

Generally, when a chip pattern is formed on a semiconductor wafer, the pattern is not always formed uniformly, but some region in the pattern exhibits a higher pattern forming density while another region in the pattern exhibits a lower pattern forming density. For example, assuming that a chip illustrated in FIG. 11 is a microprocessor, the pattern is divided, for example, into a region 1101 for memory cell circuits; a region 1102 for data input/output circuits; and a region 1103 in which no circuit pattern exists. Generally, these regions 1101, 1102, 1103 differ in circuit pattern integration degree from one another. As a result, different sizes of particles would cause failures in the respective regions. In other words, the particle size which should be managed and analyzed differs from one region to another in a chip.

Specifically stated, for example, when a particle of size α or more would cause the chip to be defective in the region 1101; a particle of size β or more in the region 1102; and a particle of size γ or more in the region 1103, information on these regions and information on particle size which causes the chip to be defective in each of these regions are previously stored in the inspection apparatus as management data. The information on the regions and information on particle size causing the defective chip may be directly entered on a screen which may be provided on the inspection apparatus for entering coordinate values and particle size, or regions may be selected from an optical image captured by a TV camera or the like. Alternatively, data may be downloaded from a higher rank system, or data may be read into the inspection apparatus from a removable storage medium, for example, a floppy disk.

By providing the inspection apparatus with the information on the regions and the information on particle sizes which cause the chip to be defective, an object under inspection is inspected. Then, a region is determined from information on the position of a detected particle in the inspection apparatus, and the information on the detected particle size is compared with the information on particle sizes which cause the chip to be defective, to determine whether or not the detected particle will cause a failure.

As a result, particles determined as a cause of failure and particles not determined as a cause of failure are displayed in different forms, such that the particles determined as a cause of failure are distinctively displayed to the user, thereby allowing the user to be immediately aware of the particles which cause a failure.

The foregoing approach will be shown in a specific manner with reference to FIGS. 12A, 12B.

A wafer shown in FIGS. 12A, 12B is displayed with the positions of detected particles 1202 indicated thereon. Since the result of detection has been displayed as shown in FIG. 12A in the prior art, an analysis on the cause of failure involves selecting proper particles and analyzing the selected particles. Therefore, the prior art suffers from a low probability that particles which should be essentially analyzed can be selected, and a long time required for the analysis on the cause of failure. On the contrary, by displaying in a different form those particles which have been determined as the cause of failure using the foregoing determination, i.e., particles 1203 which should be analyzed as shown in FIG. 12B, it is possible to readily select the particles 1203 which should be analyzed from detected particles, to increase the probability that the particles which should be analyzed can be selected, and to rapidly analyze the cause of failure. In FIG. 11, for displaying different regions in different manners, they are displayed in different patterns. Alternatively, these region may be displayed in different colors or sizes. Further alternatively, displayed particles may be limited to those which cause a failure. Also, while the foregoing embodiment divides a chip into several regions, the wafer surface may be divided, for example, in accordance with the distance from the center of the wafer to the wafer edge, and different particle sizes may be managed in different regions. Furthermore, the layout of semiconductor chips may be displayed on the wafer shape 1201.

Next, description will be made on an approach for inspecting the number of particles detected in respective regions to take countermeasures to a failure with reference to FIGS. 13 and 14.

In this example, a wafer is divided into three regions, designated Region A, Region B, Region C, in each of which the number of particles is detected. Then, the result is displayed to the user in the form of graph for each region.

For example, as shown in FIG. 13, the horizontal axis represents the particle size, and the vertical axis represents the number of detected particles, wherein different colors are allocated to Region A, Region B, Region C, respectively, the particles are displayed by size in graphical representation, and the numbers of particles falling under the same size category in the three regions are displayed side by side.

Alternatively, as shown in FIG. 14, the numbers of particles falling under the same size category may be displayed in stack.

Specifically, the three regions may be a memory cell region, a circuit region other than memory circuit, and region without circuit pattern, for example, on a semiconductor wafer. By displaying these regions as shown in FIGS. 13 and 14, the management of particles by region is facilitated. The information on the regions may be directly entered on a screen which may be provided on the inspection apparatus for entering coordinate values and particle size, or regions may be selected from an optical image captured by a TV camera or the like. Alternatively, data may be downloaded from a higher rank system, or data may be read into the inspection apparatus from a removable storage medium, for example, a floppy disk.

Next described will be an approach for counting the number of detected particles by size in each of regions to find out defective products.

As described above, the particle size determined as a cause of failure differs from one region to another. In a certain region which does not include very fine circuits, even a relatively large particle would not be regarded as a cause of failure. On the other hand, in another region which includes fine circuits, even a relatively small particle could cause a trouble. In this way, thresholds over which an alarm is generated are designated by $\alpha$, $\beta$, $\gamma$ for Region A, Region B, Region C, respectively. For example, in the example shown in FIGS. 13, 14, assume:

$\alpha=1.0$ [$\mu$m]
$\beta=1.6$ [$\mu$m]
$\gamma=2.0$ [$\mu$m]

With these thresholds, the total sum of detected particles exceeding the threshold set for each region is as follows:

Region A . . . 24
Region B . . . 3
Region C . . . 1

Even though a very large number of particles are apparently detected in Region C, they do not significantly affect the quality of a product. On the other hand, particles detected in Region A, the number of which is not so large as in Region C, is highly likely to affect the quality of the product, so that the product could be determined as defective due to the particles attached on Region A with a high probability. In this way, a reasonable inspection can be conducted in accordance with the characteristic of each region by setting a threshold of particle size for each region, over which a particle detected therein is regarded as a cause of failure, counting the total sum of detected particles exceeding the threshold in each region, determining whether the object under testing is non-defective or defective, and displaying the user to the result of determination.

[About Optical System in Apparatus for Inspecting Particles or Defects]

In the foregoing description on the present invention, the optical system in the apparatus for inspecting particles or defects employs scattered light to detect particles and measure the sizes of the particles. The approach of the present invention, however, can be applied to an optical system which relies on reflected light to detect particles or defects and measure the sizes thereof. Generally, the optical system relying on scattered light exhibits a high inspection efficiency but a low measurement accuracy. On the contrary, the optical system relying on reflected light exhibits a low inspection efficiency, but a high measurement accuracy. The approach of the present invention can be applied to either of the optical systems.

As appreciated from the foregoing, the present invention provides an apparatus and method for inspecting particles ore defects, which are suitable for use in inspecting particles or defects in processes for manufacturing semiconductor wafers or thin film substrates and conducting a failure analysis based on the inspection result. The inspection apparatus and method are capable of rapidly taking countermeasures to a failure by conducting an inspection and a failure analysis in accordance with the characteristics of particles and patterns or the characteristics of regions on an object under inspection.

The invention may be embodied in other specific forms without departing from the spirit or essential characteristics thereof. The present invention is therefore to be considered in all respects as illustrative and not restrictive, the scope of the invention being indicated by the appended claims rather than by the foregoing description and all changes which come within the meaning and range of equivalency of the claims are therefore intended to be the embraced therein.

What is claimed is:

1. An apparatus for inspecting defects comprising:
    illuminating means for irradiating light to an object under inspection;
    light detecting means for detecting reflected light or scattered light from the object under inspection;
    processing means for processing a signal output from the light detecting means to detect defects;
    classifying means for classifying said defects detected by said processing means into categories;
    dimension calculating means for processing the signal according to the classified categories to calculate a size of each defect;
    data processing means for processing an inspection result; and
    display means for displaying information on the inspection result,
    wherein the data processing means relates a defect size to a cause of failure to estimate a cause of failure from statistical processing on the inspection result, and the display means display information on the estimated cause of failure, and
    wherein said classifying means classifies said defects detected by said processing means into said categories in accordance with shape of said defects, and said dimension calculating means includes a storage unit in which a plurality of conversion curves used for calculating defect size of said defects have been stored in advance, each of curves representing relationship between intensity of light detected by said light detecting means and defect size, and being configured in accordance with shape of defect.

2. An inspection apparatus according to claim 1, wherein the display means displays a distribution of frequencies for defect sizes measured by the dimension measuring means.

3. An inspection apparatus according to claim 1, wherein the display means displays defects having a particular size in a manner discriminative from the remaining particles or defects.

4. An inspection apparatus according to claim 1, wherein the data processing means performs a failure analysis by generating management information for each of regions on the object under inspection, comparing the management information with sizes of defects detected from each region to evaluate whether each of the regions on the object under inspection is non-defective or defective in quality.

5. An inspection apparatus according to claim 4, wherein the display means displays defects having a particular size in each of the regions in a manner discriminative from the remaining defects based on an evaluation result.

6. An inspection apparatus according to claim 1, wherein the display means displays the distribution of frequencies for defect sizes measured by the dimension measuring means for each of the regions on the object under inspection.

7. An inspection apparatus according to claim 1, wherein the dimension measuring means uses an integral of a signal value detected by the light detecting means.

8. An inspection apparatus according to claim 1, wherein the dimension measuring means uses a maximum of a signal value detected by the light detecting means.

9. An inspection apparatus according to claim 1, wherein the illuminating means illuminates white light to the object under inspection.

10. A method of inspecting defects comprising the steps of:
    irradiating an object under inspection with light;
    detecting reflected light or scattered light from the object under inspection;
    processing a signal indicative of detected reflected light or scattered light to detect defects;
    classifying said defects detected by said processing into categories;
    calculating a size of each defect by processing a signal of said detected defect in accordance with said classified categories;
    processing data including data representative of the signal and including a result of measuring the size of each defect; and
    displaying the result of data processing,
    wherein the step of processing data includes estimating a cause of failure, and the step of display includes displaying information on an inspection result, and
    wherein the step of classifying includes classifying said defects into said categories in accordance withy shape of said defects and the step of calculating includes storing a plurality of conversion curves used for calculating defect size of said defects in a storage unit in advance, each of curve representing relationship between intensity of light detected by said light detecting means and defect size, and being configured in accordance with shape of defect.

11. A method of inspecting defects according to claim 10, wherein the step of displaying includes displaying a distribution of frequencies for particle or defect sizes measured by the step of measuring.

12. A method of inspecting defects according to claim 10, wherein the step of displaying includes displaying defects having a particular size in a manner discriminative from the remaining defects.

13. An inspection apparatus according to claim 1, wherein said classifying means classifies said defects into categories including particle and scratch.

14. An inspection apparatus according to claim 1, wherein said classifying means classifies said defects into categories including particles by shape.

15. A method of inspecting defects according to claim 13, wherein in said step of classifying, said categories including particle and scratch.

16. A method of inspecting defects according to claim 13, wherein in said step of classifying, said categories including particles by shape.

* * * * *